United States Patent [19]

Ferrario et al.

[11] Patent Number: 5,451,571
[45] Date of Patent: Sep. 19, 1995

[54] PROCESS AND COMPOSITION FOR TREATING HYPERTENSION

[75] Inventors: Carlos M. Ferrario, Winston-Salem, N.C.; Robson A. S. Santos, Shaker Heights, Ohio; Kay B. Brosnihan, Winston-Salem, N.C.

[73] Assignee: The Cleveland Clinic Foundation, Cleveland, Ohio

[21] Appl. No.: 345,547

[22] Filed: Nov. 28, 1994

Related U.S. Application Data

[63] Continuation of Ser. No. 845,778, Mar. 4, 1992, abandoned, which is a continuation-in-part of Ser. No. 613,955, Nov. 13, 1990, abandoned, which is a continuation of Ser. No. 259,929, Oct. 19, 1988, abandoned.

[51] Int. Cl.$^6$ .......................... C07K 5/06; A61K 38/05
[52] U.S. Cl. .............................................. 514/19; 514/18
[58] Field of Search ..................................... 514/18, 19

[56] References Cited

PUBLICATIONS

Kokubu et al., Biochemical Pharmacology, vol. 22, pp. 3217–3223 (1973).
Kono, et al., Life Sciences, 38:1515–1519, 1986.
Schiavone, et al., Proc. Natl. Acad. Sci., U.S.A., 85:4095–4098, Jun. 1988.
Ward, et al., Bioch. Pharm., 36(19):3187–3193, 1987.

*Primary Examiner*—Jill Warden
*Assistant Examiner*—Carol A. Salata
*Attorney, Agent, or Firm*—Fay, Sharpe, Beall, Fagan, Minnich & McKee

[57] ABSTRACT

The present invention is directed to a process for treating hypertension in mammals through the administration of an effective amount of a Z-Pro-prolinal (ZPP) composition. In addition, the present invention is also directed to a pharmaceutical composition for treating hypertension in mammals comprised of an active ingredient, Z-Pro-prolinal (ZPP). It has recently been discovered that Z-Pro-prolinal (ZPP) is a useful inhibitor to the biosynthetic formation of Ang(1-7), a previously unknown biologically active hypertensive agent in the reninangiotensin system (RAS). By administering an effective amount of Z-Pro-prolinal (ZPP), Ang-(1-7) formation may be reduced, resulting in a significant decrease in blood pressure without notable changes in heart rate and other circulatory functions.

12 Claims, 7 Drawing Sheets

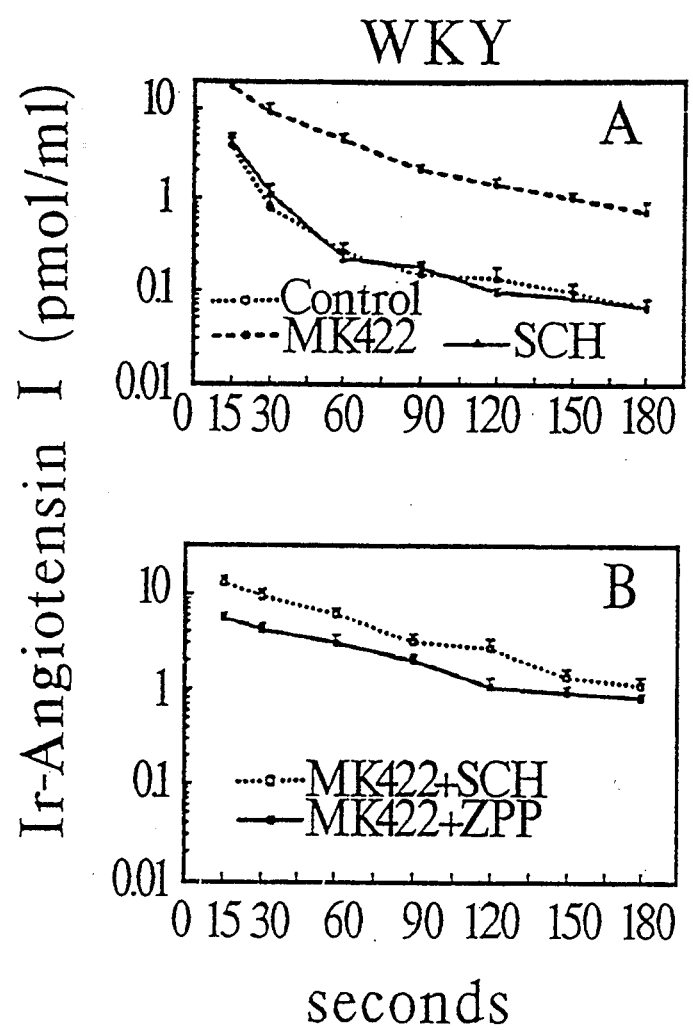
FIGURES 12A-B

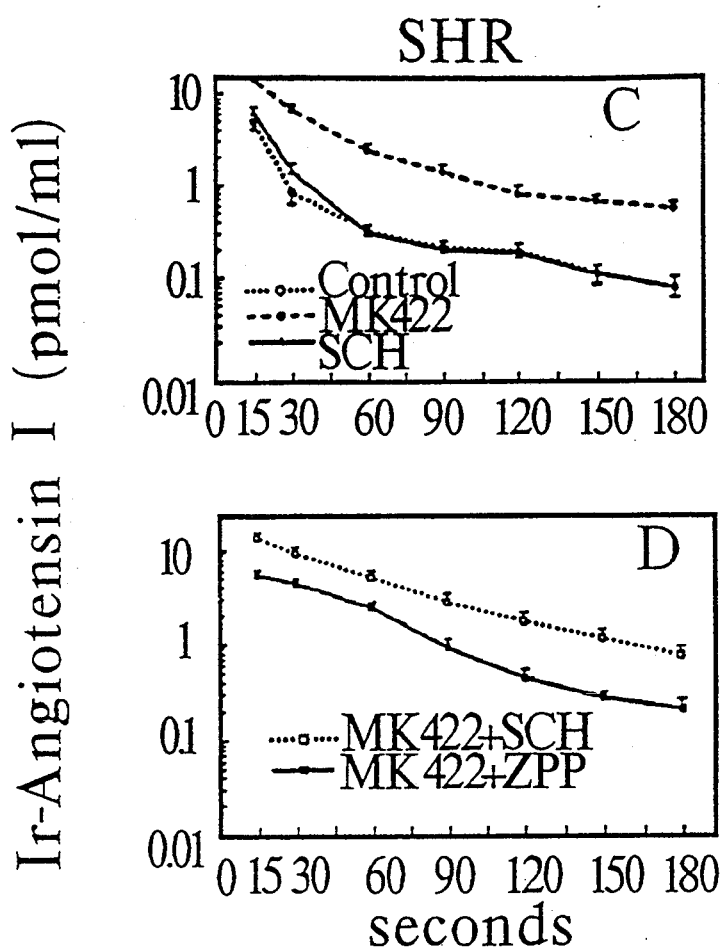
FIGURES 12C-D

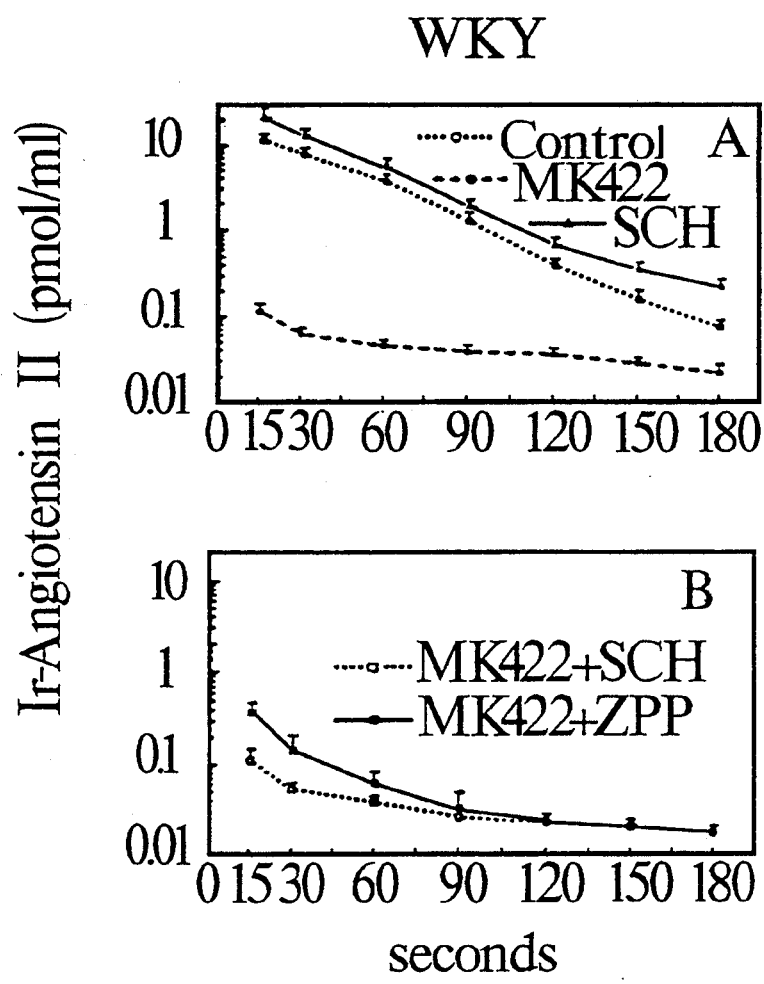
FIGURES 13A-B

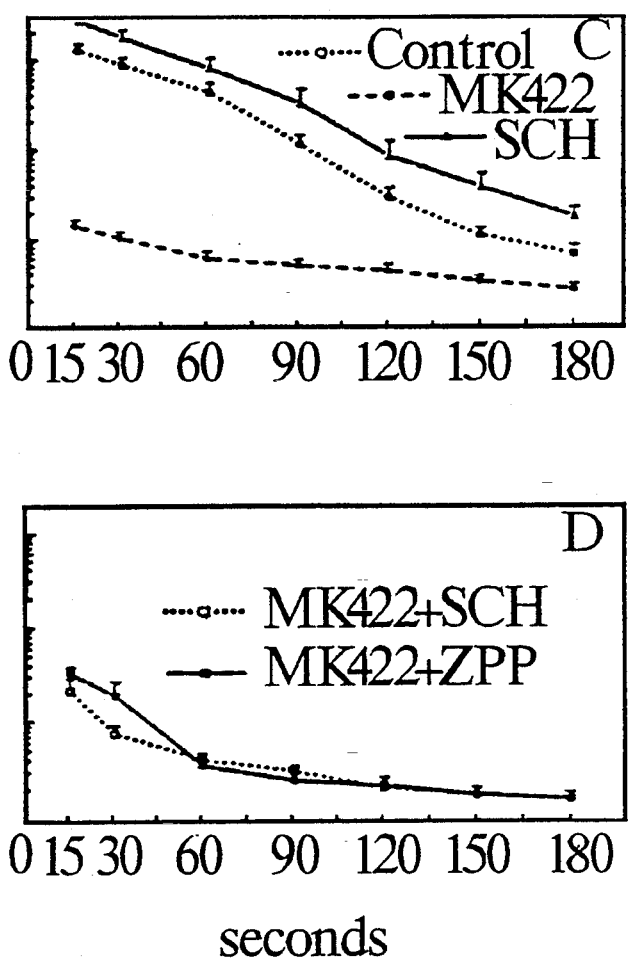
FIGURES 13C-D

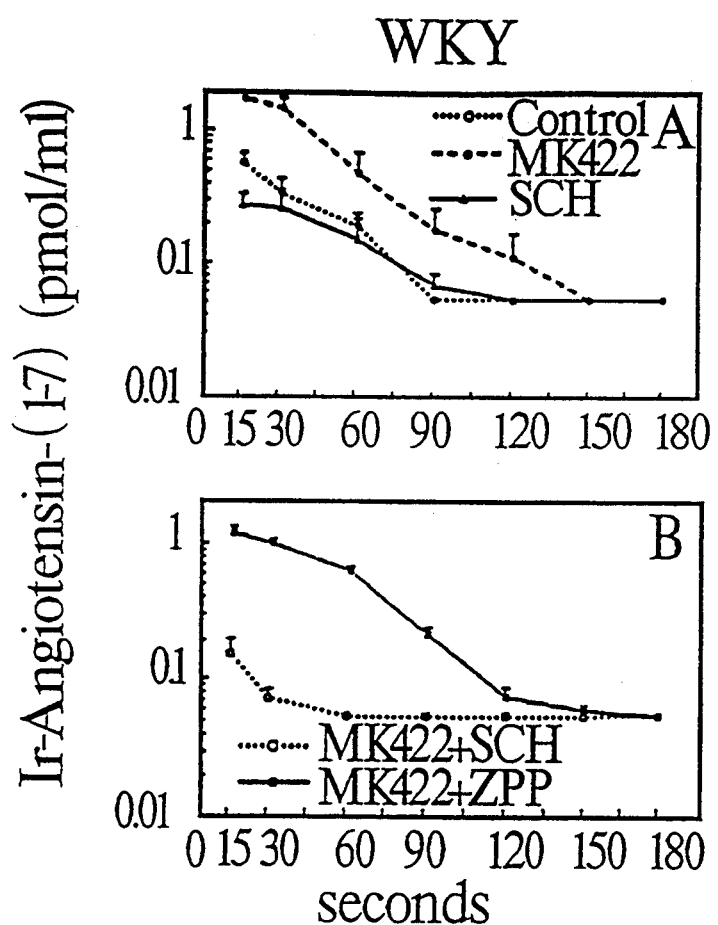
FIGURES 14A-B

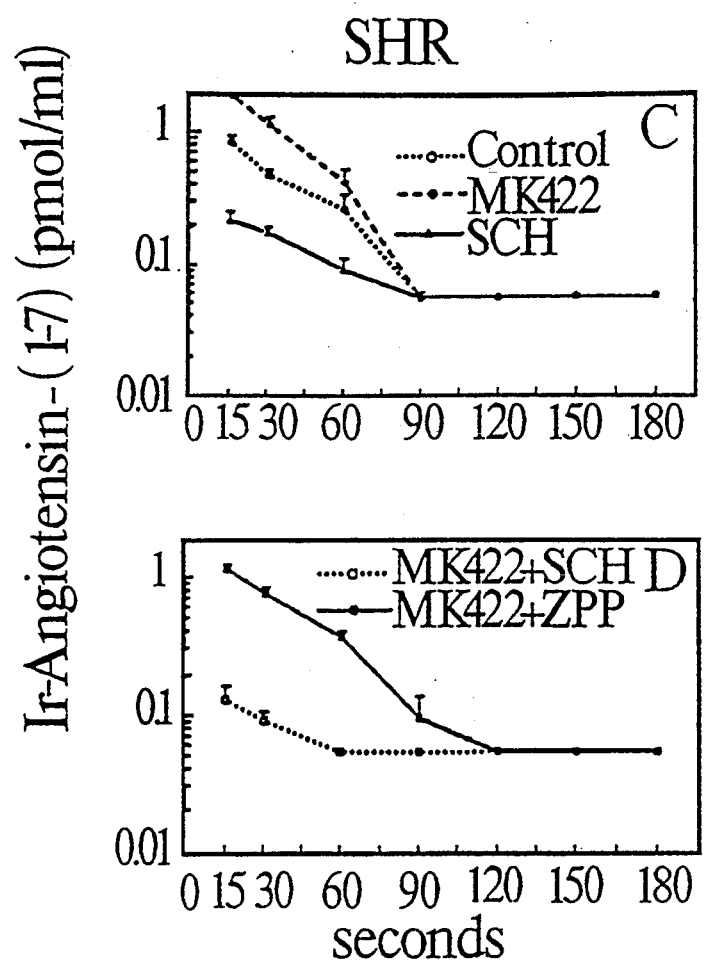
FIGURES 14C-D

PROCESS AND COMPOSITION FOR TREATING HYPERTENSION

This is a continuation of application Ser. No. 845,778 filed on Mar. 4, 1992 now abandoned; which is a continuation-in-part of application Ser. No. 613,955 filed on Nov. 13, 1990 now abandoned; which is a continuation of application Ser. No. 259,929 filed on Oct. 19, 1988 now abandoned.

BACKGROUND OF THE INVENTION

The present invention relates to a process for treating hypertension through the administration of an effective amount of a an inhibitor to the renin-angiotensin system of a mammal in order to inhibit the formation of the heptapeptide Angiotensin-(1-7). Examples of such inhibitors include Z-Pro-prolinal, N-{N-[1-(S)-carboxy-3-phenylpropyl]-(S)-phenylalanyl}-(S)-isoserine (SCH 39,370), and carboxy-phenylpropylalanine-phenylalanine-para-aminobenzoate (cFP-A-A-F-pAB). In addition, the present invention further relates to a pharmaceutical composition for treating hypertension in mammals comprised of an Angiotensin-(1-7) inhibitor as the active ingredient. In this regard, inhibitors such as Z-Pro prolinal have recently been discovered by the present inventors inhibit the formation of the heptapeptide Angiotensin-(1-7) [Ang-(1-7)], an N-terminal fragment of Angiotensin II (Ang II) previously considered to be an inert product of the renin-angiotensin system (RAS). Through the administration of an inhibitor such as an effective amount of a Z-Pro-prolinal (ZPP) composition, Ang-(1-7) formation is inhibited and the blood pressure in mammals can be controlled without notable changes in heart rate and other circulatory functions.

The renin-angiotensin system (RAS) is an important regulatory system for controlling blood pressure in mammals. Although the voluminous literature on the biochemical pathways and physiological actions of the renin-angiotensin system (RAS) contains notable controversies, it has never been questioned that the octapeptide Angiotensin II (Ang II) is the biologically active principle of the RAS. In this regard, it has generally been assumed that the interaction of Ang II with specific receptors found on several organs produces the systematic effects related to the control of blood pressure. The most prominent of the effects produced by circulating Ang II is the direct vasoconstriction of the peripheral vasculature, which is normally accompanied by a variety of changes in kidney functions such as alterations in the glomerular filtration rate, tubular reabsorption, and renal arteriolar resistance.

Moreover, not only is Ang II's function in the peripheral tissue as a plasma hormone well known, its biosynthetic pathway for formation has also been well documented. The following steps are generally stated to be the pertinent steps in the formation of Ang II in the RAS:

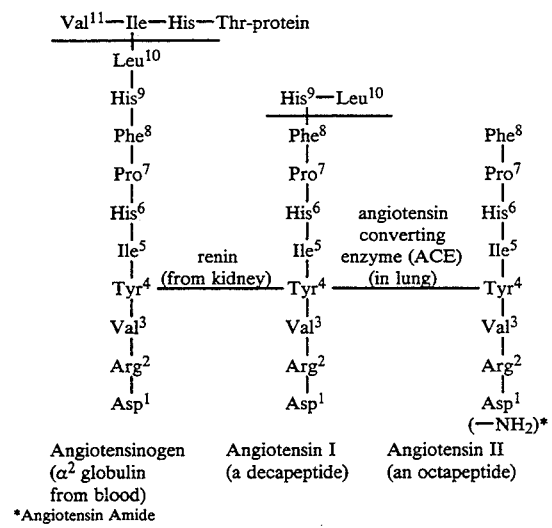

Angiotensinogen ($\alpha^2$ globulin from blood)   Angiotensin I (a decapeptide)   Angiotensin II (an octapeptide)

*Angiotensin Amide

The production of Ang II from the polypeptide precursor, Angiotensinogen, is regulated by two proteolytic enzymes, renin and angiotensin converting enzyme (ACE), which cleave successively at the $Leu^{10}$-$Val^{11}$ and $Phe^8$-$His^9$ bonds to produce Angiotensin I (Ang I) and Ang II, respectively. Renin occurs predominantly in the juxtaglomerular cells of the kidney but has also been detected at a number of extrarenal sites. ACE, a dipeptidyl-carboxypeptidase, is normally present in the serum; the endothelial cells of the pulmonary vascular bed; and also in many other tissues such as the kidney, gut, brain, and testis. The combined efforts of the kidney to produce renin when a decrease in blood pressure is detected, of the liver to produce the renin substrate, Angiotensinogen (Aogen), found in the circulating blood (which is cleaved by the renin to form Ang I) and of the lungs to produce the ACE (which converts the Ang I to Ang II) are all required for the generation of the biologically active peptide Ang II in the peripheral tissues.

The generated Ang II in turn increases blood pressure by constricting blood vessels and by activating aldosterone secretion which stimulates sodium retention (and potassium wasting) by the renal tubule. In addition, it is also thought that Ang II induces thirst and arginine vasopressin (AVP) release in the systemic system.

Furthermore, while renin and ACE play critical roles in the processing of Angiotensinogen (Aogen) to Ang II, other endo- and carboxypeptidases are thought to contribute as well to the formation of Ang II and/or Ang II analogs such as Ang-(2-8), Ang-(1-7), etc. Studies of the in vivo and in vitro catabolism of Angiotensin peptide precursors, and of Ang II in tissues, suggest that some of the C-terminal fragments formed through metabolism of Ang I and Ang II may be bioactive.

In addition, although other angiotensin fragments and/or analogs of Ang II derived from the aminoterminus (N-), such as Ang-(1-7), have been isolated and purified (i.e. enzymes which cleave peptides at the Proline-Phenylalanine bond exist in many tissues), it has generally been concluded from studies of the structure-activity relationship in Ang II analogs, that fragments of Ang II lacking an aminoacid residue in position 8 of the polypeptide are inert. Along the same lines, it is widely believed in the art that the phenyl group in position 8 contains the information necessary for regulating blood pressure in mammals.

In this regard, while Yang, et al. first showed the generation of an N-terminal fragment of Ang II [the heptapeptide Angiotensin-(1-7)] in swine and human urine (Yang, H. Y. T., Erdos, E. G., and Chang, T. S., *New Enzymatic Route for the Inactivation of Angiotensin*, Nature 218: 1224–1226, 1968), and similar findings were obtained by Regoli, et al. in vascular smooth muscle (Regoli, D., Park, W. K., Rioux, F., and Magnan, J., *Metabolism of Angiotensin in Vascular Smooth Muscle: In Biologically Active Peptides*. R. Waher & J Meienh, (eds.). Ann Arbor, Mich.; Ann Arbor Sci. Publishers, Inc., pp: 617–624, 1975), by Tonnaer, et al. in preparations of synaptic membranes from the rat brain (Tonnaer, J. A., Wiegant, V. M., DeJong, W., and DeWied, D., *Central Effects of Angiotensins on Drinking and Blood Pressure: Structure—Activity Relationships*, Brain Res. 236: 417–428, 1982; and, Tonnaer, J. A., Engles, G. M., Wiegant, V. M., Burbach, J. P., DeJong, W., and Diewied, D., *Proteolytic Conversion of Angiotensins in Rat Brain Tissue*, Eur. J. Biochem., 131: 415–421, 1983), and by Allard, et al. in cultured mouse spinal cord cells (Allard, M., Simonnet, G., Dupouy, B., and Vincent, J. D., *Angiotensin II Inactivation Process in Cultured Mouse Spinal Cord Cells*, J. Neurochem. 48: 1553–1559, 1987), pharmacological studies showed that the Ang-(1-7) did not elicit contractile responses in isolated vessels and/or demonstrate the pressor, dipsogenic, or aldosterone stimulating properties of Ang II. From these studies it was concluded that fragments of Ang II derived from the amino terminus (N-), such as Ang-(1-7), have no biological activity.

Moreover, although it has been generally assumed that the RAS maintains blood pressure through Ang II generated in the circulation, recent evidence clearly indicates the existence of a separate renin-angiotensin system (RAS) in the brain of mammals (i.e. brain RAS). The evidence which supports the finding of a separate brain renin-angiotensin system (RAS) includes the following:

(a) the finding of a biosynthetic pathway for Ang II formation which includes Angiotensinogen and multiple enzymatic activities with the potential for forming angiotensin peptides;

(b) neuronal sites where immunocytochemically identified Ang II has been localized;

(c) the extraction of Ang II from brain tissue and its identification by high pressure liquid chromatography (HPLC); and, (d) angiotensin receptors demonstrated both by traditional membrane binding assay as well as by receptor autoradiography.

The discovery that neuronal elements in the brain produce Ang II has evinced Ang II's role as a regulatory neuropeptide in the central pathway subserving the maintenance of hydromineral balance and circulatory function. Although studies have shown that fragments containing the C-terminal sequence of Ang II mimic actions of the parent hormone in causing drinking (Fitzsimons, J. T., *The Effect on Drinking of Peptide Precursors and of Shorter Chain Peptide Fragments of Angiotensin II Injected into the Rat's Diencephalon*, J. Physiol. 214: 295–303, 1971; and Wright, J. W., Sullivan, M. J., Quirk, W. S., Batt, C. M. and Harding J. W., *Heightened Blood Pressure and Drinking Responsiveness to Intracerebroventricularly Applied Angiotensins in the Spontaneously Hypertensive Rat*, Brain Res. 420: 289–294, 1987), vasopressin (AVP) secretion (Fyhrquist, F., Eriksson, L., and Wallenius, M., *Plasma Vasopressin in Conscious Goats After Cerebroventricular Infusions of Angiotensins, Sodium Chloride, and Fructose*, Endocrinology 104: 1091–1095, 1979), increases in blood pressure (Fink, G. D. and Bruner, C. A., *Hypertension During Chronic Peripheral and Central Infusion of Angiotensin III*, Am. J. Physiol. 249: E201–E208, 1985; and Yang H. Y. T., Erdos, E. G., and Chiang, T. S., *New Enzymatic Route for the Inactivation of Angiotensin*, Nature 218: 1224–1226, 1986) and excitation of rat paraventricular (PVN) neurons (Harding, J. W., and Felix, D., *Angiotensin-Sensitive Neurons in the Rat Paraventricular Nucleus: Relative Potencies of Angiotensin II and Angiotensin III*, Brain Res. 410: 130–134, 1987), the view that Ang II is the active principle of the RAS has prevailed.

While the brain and peripheral renin-angiotensin systems are independent and kept apart by the blood-brain barrier (BBB), the two systems appear to be actively involved in the control of systemic blood pressure and the development and maintenance of hypertension. More particularly, in the central nervous system, Ang II may participate in the central regulation of blood pressure by augmenting sympathetic and parasympathetic efferent discharges, by the release of arginine vasopressin (AVP) and corticotropin releasing factor (CRF) and by stimulating thirst. It is generally thought that brain Ang II is synthesized in the supraoptic nucleus and paraventricular nuclei. Because of the connections of these nuclei to circumventricular organs and median preoptic area, there is a circuitry involving Ang II to produce increased vasopressin and sympathetic activity while simultaneously inhibiting the baroreflex. These three factors are thought to act in parallel to raise blood pressure.

Furthermore, in an attempt to regulate and/or control the blood pressure produced by the brain and/or peripheral renin-angiotensin systems, a number of enzyme inhibitors of the RAS, such as renin inhibitors (i.e. synthetic phosphatidyl ethanolamine) and converting enzyme inhibitors (i.e. captopril or teprotide) have been developed and introduced into hypertension therapy to reduce the production of Ang II by the RAS. In addition, receptor antagonists, such as antagonists for Ang II receptors (i.e. saralasin) have also been utilized in order to regulate the blood pressure of mammals.

The mechanism of action of the ACE inhibitors, such as the nonsulfahydryl converting enzyme inhibitors MK-421 and its active diacid form, MK-422, produced by Merck Sharpe and Dohme, U.S.A., is presumed to be the inhibition of angiotensin converting enzyme (ACE) in the RAS at the point where Ang I is converted to Ang II. However, recent evidence questions the overall effectiveness of the angiotensin converting enzyme (ACE) inhibitors in reducing hypertension. Moreover, since ACE has a peptidyldipeptidase action on several neuropeptidases which have also been found in the brain in addition to Ang II, i.e. bradykinin, enkephalin, and luteinizing releasing hormone, use of enzyme inhibitors such as MK-421 and MK-422 may not be specific for treatment of all hypertensions.

Notwithstanding the above, the present invention is directed to the use of Z-Pro-prolinal (ZPP), an inhibitor for proyl endopeptidase, for decreasing the rate of Ang-(1-7) inhibitors such as Ang-(1-7) and/or related N-terminal fragments production, thereby reducing and/or regulating hypertension. The present invention is based on the recent findings that (1) although it had been previously concluded that among the numerous analogs of Ang II the phenylalanine group at position 8 possesses the information for biological response and thus, Ang(1-7) was inactive, applicants lave recently discovered that Ang(1-7) is as potent as Ang II in stimulating vasopressin (AVP) secretion in the brain; and, (2) certain compositions such as ZPP, SCH 39, 370 and cFP-A-A-F-pAB are effective inhibitors of the formation of Ang-(1-7) from Ang I and/or Ang II; and (3) ZPP, when administered to genetic hypertensive mammals causes a significant decrease in mean arterial pressure which is unaccompanied with any significant changes in heart rate and other circulatory functions.

SUMMARY OF THE INVENTION

In one aspect, the present invention relates to a process for treating hypertension in mammals, including the steps of providing a Z-Pro-prolinal composition or a fundamentally related drug and administering an effective amount of the Z-Pro-prolinal composition to a hypertensive mammal to reduce hypertension.

In another aspect, the present invention concerns a process for controlling blood pressure in mammals which includes the steps of administering an effective amount of Z-Pro-prolinal composition to a mammal to reduce the blood pressure of the mammal.

In an additional aspect of the invention, the present invention concerns a composition for treating hypertension comprising Z-Pro-prolinal.

In a further aspect of the invention, the present invention relates to a composition for treating hypertension comprised of an active ingredient, Z-Pro-prolinal.

In still another aspect of the invention, the present invention concerns a pharmaceutical composition for treating hypertension in mammals, which comprises one or more pharmaceutically acceptable excipients, and an amount of Z-Pro-prolinal or a fundamentally related drug effective to treat hypertension in mammals.

In a still further aspect of the invention, the present invention relates to a pharmaceutical composition for treating hypertension in mammals which comprises one or more acceptable excipients, and an amount of Z-Pro-prolinal per unit weight of said composition effective to treat hypertension in a mammal to whom one or more unit doses of said composition are administered.

DESCRIPTION OF THE DRAWINGS

The following is a brief description of the drawings which are presented for the purpose of illustrating the invention and not for the purpose of limiting same.

FIGS. 1A, 1B, and 1C are graphs demonstrating the regional rostrocaudal distribution of angiotensin converting enzyme (ACE) activity in relation to the content of norepinephrine (NE) and serotonin (5-HT) in the dorsal and ventral regions of the dog brainstem.

FIGS. 2A, 2B, 2C, and 2D are high performance liquid chromatography (HPLC) profiles of $^{125}$I-labelled products produced from labelled Ang I incubated with a brain punch homogenate from the A2 region (obex level). FIG. 2A represents the HPLC elution profile of 125I-labelled angiotensin peptides (standards). FIGS. 2B, 2C, and 2D illustrate products obtained from the incubation of $^{125}$I-Ang I with the brain punch homogenate at two, five, and fifteen minutes, respectively.

FIGS. 3A and 3B are high performance liquid chromatography (HPLC) profiles demonstrating the effect of ACE inhibition on the metabolism of $^{125}$I-Ang I by a brain punch homogenate from the A2 region (obex level). $^{125}$I-Ang I was incubated with the brain punch homogenate for five minutes in the absence (FIG. 3A) or presence (FIG. 3B) of 50 mM MK 422.

FIG. 4 is a graph demonstrating the dose-related increase in arginine vasopressin (AVP) from the rat hypothalamo-neurohypophysial system caused by Ang(1-7) and Ang II.

FIGS. 5A and 5B are graphs which illustrate the effect of [Sar$^1$, Thr$^8$] Ang II before and during the concomitant addition of either Ang-(1-7) (FIG. 5A) or Ang II (FIG. 5B).

FIGS. 6A and 6B are graphs which indicate changes in mean arterial pressure (FIG. 6A) and heart rate (FIG. 6B) produced by microinjections of Ang-(1-7) into the nucleus tractus solitarii (nTS) where individual dots represent 37 injection sites in 31 rats, and the bars represent the group means±SEM.

FIGS. 7A and 7B are graphs which illustrate changes in mean arterial pressure (FIG. 7A) and heart rate (FIG. 7B) produced by microinjections of Ang-(1-7) into the dorsal motor nucleus of the vagus (dmnX) where individual dots represent 15 injections sites in 14 rats, and the bars represent the group means±SEM.

FIGS. 8A and 8B are graphs indicating the change in mean arterial pressure (mm Hg) with time (min) in normotensive Wistar-Kyoto control rats (WKY-FIG. 8A) and in spontaneously hypertensive rats (SHR-FIG. 8B).

FIGS. 9A and 9B are graphs illustrating the relationship between changes in heart rate (beats/min) and time (min) in normotensive Wistar-Kyoto control rats (WKY-FIG. 9A) and in spontaneously hypertensive rats (SHR-FIG. 9B).

FIGS. 10A and 10B are bar graphs indicating the effects produced by an administration of a depolarizing concentration of K+ on mean arterial pressure (mm Hg) in normotensive Wistar-Kyoto control rats (WKY-FIG. 10A) and in spontaneously hypertensive rats (SHR-FIG. 10B).

FIGS. 11A and 11B are bar graphs illustrating the effects produced by an administration of a depolarizing concentration of K+ on heart rate (beats/min) in normotensive Wistar-Kyoto control rats (WKY-FIG. 11A) and in spontaneously hypertensive rats (SHR-FIG. 11B).

FIGS. 12A, 12B, 12C and 12D are time concentration curves of angiotensin I in the blood of Wistar Kyoto (WKY) and spontaneously hypertensive rats (SHR) produced by intravenous injection of 2 nmol of angiotensin I. Values are means±SE. Abbreviations are, MK 422, enalaprilat; SCH, is the neutral endopeptidase 24.11 inhibitor SCH 39,370; ZPP, Z-pro-prolinal, a specific inhibitor of prolyl endopeptidase.

FIGS. 13A, 13B, 13C and 13D are time concentration curves of angiotensin II in the blood of Wistar Kyoto (WKY) and spontaneously hypertensive rats (SHR). Values are means±SE. The other abbreviations are the same as in FIGS. 12A-12D.

FIGS. 14A, 14B, 14C and 14D are time concentration curves of angiotensin-(1-7) in the blood of Wistar Kyoto (WKY) and spontaneously hypertensive rats (SHR). Values are means±SE. The other abbreviations are the same as in FIGS. 13A-13D.

DETAILED DESCRIPTION OF THE INVENTION

Figure 15:
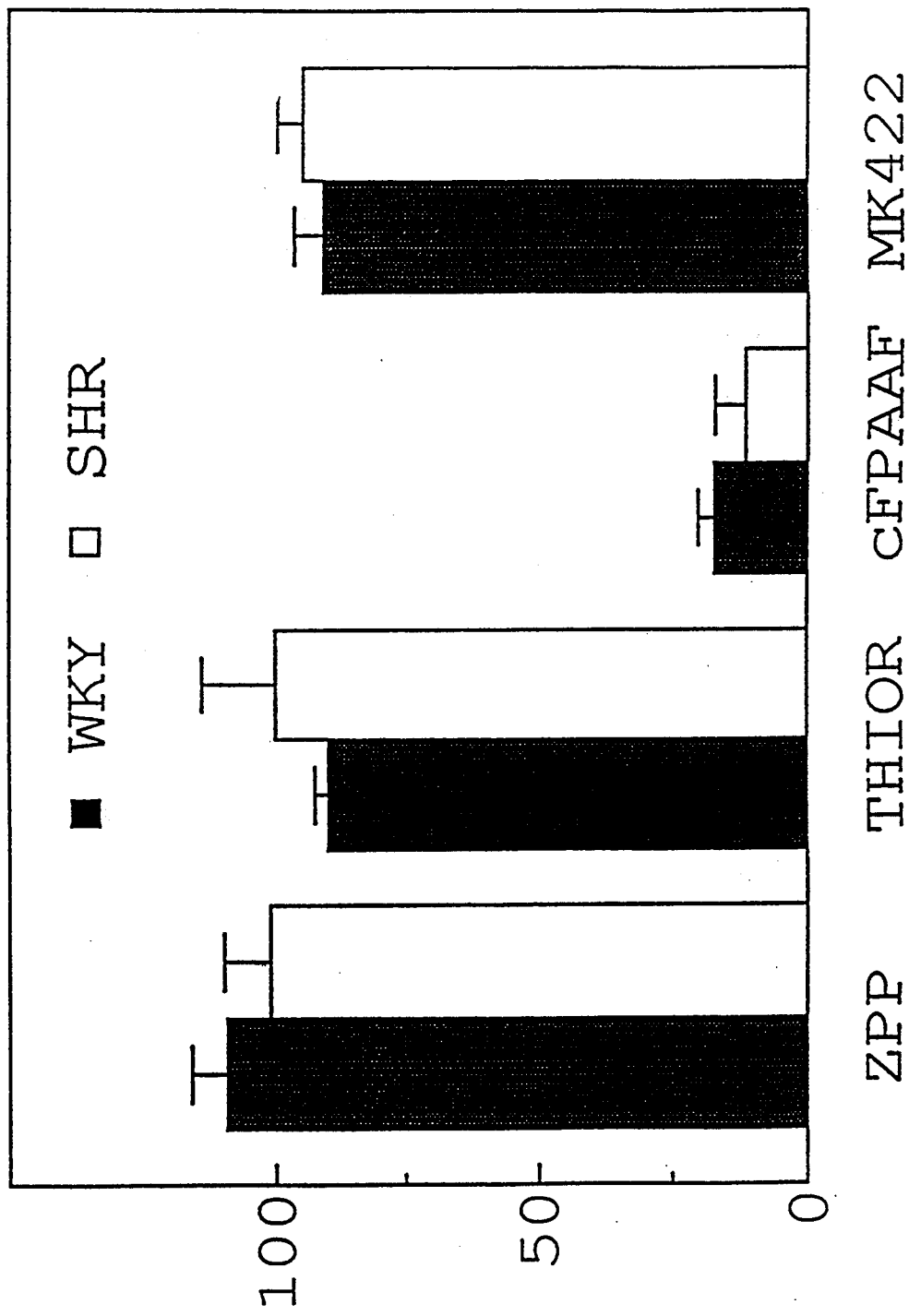
FIG. 15 is a bar graph demonstrating the effect of various inhibitors on the levels of $^{125}$I-Ang(1-7) from vascular smooth muscle cultures of spontaneously hypertensive (SHR) and normotensive (WKY) rats.

The present invention is directed to a process for treating hypertension in mammals through the administration of an effective amount of a Z-Pro-prolinal (ZPP) composition. In addition, the present invention is also directed to a pharmaceutical composition for treating hypertension in mammals comprised of an active ingredient Z-Pro-prolinal (ZPP) additional Ang-(1-7) inhibitors such as N-{N-[1-(S)-carboxy-3-phenylpropyl]-(S)-phenylalanyl-(S)-isoserine (SCH 39,370) and carboxyphenyl propyl-alanine-alaninephenylalanine-para-aminobenzoate (cFP-A-A-F-pAB). It has recently been discovered by the present inventors that Z-Pro-prolinal (ZPP) SCH (39,370 and cFP-A-A-F-pAB are useful inhibitors to the biosynthetic formation of Ang(1-7), a previously unknown biologically active hypertensive agent in the renin-angiotensin system (RAS). By administering an effective amount of an Ang-(1-7) inhibitors such as Z-Pro-prolinal (ZPP), Ang-(1-7) formation may be reduced, resulting in a significant decrease in blood pressure without notable changes in heart rate and other circulatory functions.

The following examples describe the procedure utilized by the present inventors in discovering the bioactivity of Ang-(1-7), as well as the specific practice of the instant invention concerning use of an effective amount of Z-Proprolinal for treating hypertension in mammals:

cl EXAMPLE 1

Evidence that Ang-(1-7) is the major product generated from Ang I in the presence and absence of ACE inhibition In order to expand upon the current understanding of the brain renin-angiotensin system (RAS) and the role the catecholamine neuronal groups of the dorsal and ventral brainstem and the spinal cord have in blood pressure regulation, the distribution of angiotensin converting enzyme (ACE) in these areas of the dog were studied. In addition, the proteolytic hydrolysis of Ang I in brain punch homogenates of the dog's brainstem and spinal cord were studied to evaluate the biochemical pathways that account for the generation and metabolism of angiotensins in the brain.

Materials and Methods

Experiments were performed on fourteen mongrel dogs weighing 16±2 kg and anesthetized with sodium pentobarbital (30 mg/kg i.v.). Arterial and venous catheters (Tygon, Faultless Rubber Co., Ashland, Ohio, USA), were inserted in a femoral artery and vein for the removal of blood. Ten of the fourteen dogs were given a lethal dose of sodium pentobarbital, and the brain and thoracic portion of the spinal cord (C6-T3) were excised immediately. The brain was removed from four other dogs six hours after a single injection of MK 422 (enalaprilat) at a dose of 10 mg/kg i.v.

Tissues were partially frozen on dry ice and placed on a prechilled tissue slicer, modified from that described by Palkovits and Brownstein (Palkovits, M., Brownstein, M. J. *Microdissection of Brain Areas by the Punch Technique*, In: Cuello AC, ed., Brain micro-dissection technique, New York: John Wiley & Sons, 1983: 1–36). A microtome knife (A. H. Thomas, Philadelphia, Pa., USA) was situated at the obex; additional blades (set 2 mm apart) provided uniform serial sections from 6 mm caudal to the obex to the level of the inferior colliculus. Coronal sections (2000 µm thick) from either the brainstem or the spinal cord were laid on a frozen Petri dish placed under the operating microscope. Plugs of tissue were removed using a punch technique (Palkovits, et al. supra) (13–15 gauge needle) throughout the rostrocaudal extension of structures that were shown by fluorescent histochemistry (Chernicky, C. L., Barnes, K. L., Ferrario, C. M., Conany, J. P. *Catecholaminergic Pathways of the Dog Brainstem*, Neurosci. Abstr. 1984; 10:62) to belong to the catecholamine neuronal groups described in the rat (Dahstrom, A., Fuxe K., *Evidence for the Existence of Monoamine Containing Neurons in the Central Nervous System: In. Demonstrating of Monoamines in the Cell Bodies of Brainstem Neurons*, Acta Physiol. Scand. 1964; 62:1–55). Punches were obtained from (1) the A1 region in the ventrolateral medulla from the pyramidal decussation to the rostral pole of the inferior olive; (2) the A2 region, which includes the dorsal motor nucleus of the vagus nerve (dmnX), the nucleus of the tractus solitarius (nTS), and the solitary tract, between −6 mm and +10 mm from the obex; (3) the A5 region, which is dorsal to the superior olive and medial to the seventh nerve, between +14 and +16 mm from the obex; and (4) the A6 region on the dorsolateral pontine tegmentum (locus ceruleus) from +18 mm to +22 mm from the obex. Punches from coronal sections of the intermediolateral column of the spinal cord were obtained between C6 and T3. Blocks of tissue were also taken from the area postrema at the obex, the neurohypophysis, and the choroid plexus in the fourth ventricle. Remaining coronal tissue sections were analyzed separately. All tissue samples were kept on dry ice and stored at −70° C. until assayed.

The ACE activity and angiotensin metabolism were measured in tissue samples obtained from five control and four MK 422-treated dogs. Five other dogs were used to determine the content of norepinephrine (NE) and serotonin (5-HT) in the same regions used to characterize the activity of the ACE.

Tissue punches (1–5 mg wet weight) were homogenized using a glass homogenizer (Kontes Scientific Glassware, Vineland, N.J., USA) in 140 µl of 50 mM sodium borate buffer, pH 8.3, containing 112 mM NaCl and 0.1% Triton X-100. Larger tissue samples were homogenized to a final concentration of 100 mg tissue ml/buffer. The homogenates were centrifuged at 18,000 g for two minutes at 4° C. The ACE activity was determined by incubating 10 µl of the supernatants with 500 µl of an assay solution containing 5 mM Hip-His-Leu (Sigma Chemical, St. Louis, Mo., USA) in 0.4 M sodium borate buffer, pH 8.3, and 0.9 M NaCl for 15 minutes at 37° C.) (Santos R. A. S., Krieger, E. M., Greene, L. J., *An Improved Fluorometric Assay of Rat Serum and Plasma Converting Enzyme*. Hypertension 1985; 7:244–252). The product His-Leu was measured fluorometrically (365 nm excitation, 495 emission; Aminco spectrofluorometer, American Instruments, Silver Springs, Md., USA). In punches obtained from the brainstem, neurohypophysis, and choroid plexus, the rate of reaction was linear over a 20-minute period and with the volume of the sample assayed (5–15 ul). Under these conditions, hydrolysis of the product His-Leu (Sigma) was less than 6% as evaluated indirectly fluorometry (Santos, et al. supra). The specificity of the hydrolysis of the substrate as a measure of ACE activity was demonstrated by a 98% inhibition of product released in the presence of either 10 µM MK 422 or 1 mM EDTA. Tissue ACE specific activity was expressed as units corresponding to 1 nmol/min/mg protein. The concentration of proteins in the homogenates was determined by the method of Lowry, et al. (Lowry, O. H., Rosebrough, N. G., Farr, A. L., Randall, R. J., *Protein Measurement with the Folin Phenol Reagent*. J. Biol. Chem. 1951; 193:265-272).

To study the metabolism of angiotensin in brain punch homogenates, $^{125}$I-labelled Ang I and Ang II (New England Nuclear, Boston, Mass., USA) were purified initially to remove the peptidase inhibitor trasylol by reverse phase high performance liquid chromatography (HPLC) using a Nova-Pak C column (Waters Associates, Milford, Mass., USA). Peptides were eluted isocratically with 33.6% acetonitrile (Burdick and Jackson, American Scientific Products, Columbus, Ohio, USA) in 0.13% heptafluorbutyric acid (HFBA; Sequenal grade, Pierce, Rockford, Ill., USA) at a flow rate of 1 ml/min. The effluent (0.25 ml/fraction) was collected in tubes precoated with bovine serum albumin (BSA; Pentex, Miles Scientific, Naperville, Ill., USA). After evaporation in a vacuum centrifuge (Savant, Farmingdale, N.Y., USA), the purified peptides were redissolved in water.

The metabolism of $^{125}$I-Ang I and $^{125}$I-Ang II was studied by incubating 10 μl of brain homogenates with 190 μl of an assay solution containing 50 pM labelled standards in 20 mM Tris HCl buffer, pH 7.5, and 0.01% BSA for 2 to 15 minutes at 37° C. The reactions were stopped by the addition of 100 μl of 32% acetonitrile containing 0.13% HFBA, followed by centrifugation at 18,000 g for 2 minutes. Samples were then submitted to HPLC (Model 2150, LKB Instruments, Gaithersburg, Md., USA) using a gradient of 0.13% HFBA (vol/vol in water, Buffer A) and 80% acetonitrile containing 0.13% HFBA (Buffer B). The gradient conditions were 32% Buffer B, 5 minutes; 32 to 43%, 5 to 20 minutes; 43 to 48%, 20 to 25 minutes; and 48%, 25 to 30 minutes at a flow rate of 1 ml/min. The eluate was collected in 0.25-ml fractions.

Products of angiotensin metabolism were identified by comparison of their retention times with those of purified $^{125}$I-Ang I and $^{125}$I-Ang II, and with standards of $^{125}$I-angiotensin fragments. Labeled standards were prepared by iodination of synthetic Ang-(2-10) and Ang-(1-7) or by enzymatic hydrolysis of labeled Ang I, Ang II, and Ang-(2-10) with carboxypeptidase Y (Pierce Chemicals, Rockford, Ill., USA), chymotrypsin (AMERESCO, Solon, Ohio, USA), or trypsin-TPCK (Sigma). The incubation was made at 37° C. in 150 μl of 10 mM sodium phosphate buffer, pH 6.0, for carboxypeptidase Y (0.25 U) and 10 mM Tris HCl, pH 7.5, for trypsin and chymotrypsin (5 μg). Peptide standards obtained by more than one method were verified to elute at the same position but not to coelute with each other under the HPLC conditions reported here. The recovery after HPLC of $^{125}$I as $^{125}$I-Tyr or $^{125}$I-labeled peptides was 96±5% for the punch hydrolystate experiments.

Plasma ACE activity was measured fluorometrically (Santos, et al. supra), and plasma renin activity (PRA) and immunoreactive Ang II (irAng II) were measured by radioimmunoassay (Brosnihan, K. B., Diz, D. I., Schiavone, M. T., Averill, D. A., Ferrario, C. M., *Approaches to Establishing Angiotensin II as a Neurotransmitter*. In: Buckley, J. P., Ferrario, C. M., eds. *Brain Peptides and Catecholamines in Cardiovascular Regulation*. New York: Raven Press, 1987: 313-328). The concentrations of NE and 5-HT in brain punches were determined with an HPLC-electrochemical detection system (Brosnihan, K. B., Navickas, J., Bridle, P., Smeby, R. R., Ferrario, C. M., *Distribution of Catecholamines, Serotanin, and Their Metabolites with Discrete Regions of Dog Brains*, Int. Electroanal. T. Symp., 1986; 7: 153-156). All values are reported as means±SE. Statistical differences were evaluated by analysis of variance followed by either the Newman-Keuls or the Dunnett's multiple-range test. Hormonal changes were analyzed with Student's t test (nonpaired method). Differences were considered significant at a p value below 0.05.

RESULTS

The region rostrocaudal distribution of ACE activity in relation to the content of NE and 5-HT in the dorsal and ventral regions of the dog brainstem are shown in FIGS. 1A-1C. Tissue punches from the dorsomedial medulla in the A2 region rostral to the obex showed a high content of NE while punches obtained from the ventral medulla (A1) showed comparatively more uniform and lower levels than those measured in the dorsomedial between +2 and +6 mm from the obex (see FIG. 1B). A peak of 5-HT activity was located in the dorsomedial medulla immediate to the obex (see FIG. 1C) and in the rostral aspects of the A1 region. As reported in other species (Dahlstrom, et al. supra), punches from the locus ceruleus region showed a high content of NE and appreciable quantities of 5-HT (see FIGS. 1B and 1C).

The ACE activity in all monoamine-containing regions was at least 3.75-fold higher than the values recorded in remaining coronal tissue sections of the brainstem (5.3±0.8 U). A peak of ACE activity was found the dorsomedial medulla adjacent to the obex, while the peak in the A1 region was located rostrally between +10 and +12 mm of the obex. Enzyme activity correlated only with 5-HT concentrations in both the A2 (r=0.74) and A1 (r=0.90) regions (p is less than 0.02 and p is less than 0.0005, respectively). Both the A5 and locus ceruleus regions contained high ACE activity comparable in magnitude to that found in the choroid plexus (27.7±3.5 U). In contrast, the levels of ACE activity in the area postrema (2.45±1.47 U) and the neurohypophysis (1.28±0.12 U) were similar to those measured in remaining tissues of the brainstem (see FIG. 1A). In the intermediolateral column of the spinal cord, ACE activity averaged 10.6±2.5 U, a value twofold higher than that measured in remaining spinal cord tissue (5.5±1.1 U).

The finding of high ACE activity in brainstem structures involved in autonomic function led to a further investigation into the effect of i.v. injection of MK 422 on the activity of the enzyme in the dog brain. In dogs given MK 422 six hours earlier, ACE activity in the A2 region (between −2 and +4 mm of the obex) fell to 16.7±1.7 U compared with 22.5±1.6 U (p is less than 0.05) in untreated controls. In contrast, ACE activity in other regions of the brainstem did not change. The level of ACE activity in homogenates from the choroid plexus of dogs given MK 422 was reduced to 14.9±0.6 U, 46% lower than the levels found in untreated dogs. Comparative measurements of ACE, PRA, and irAng II in the plasma six hours after injection of MK 422 confirmed that blockade of plasma ACE activity (2.1±0.2 vs. 17.7±1.6 nmol/ml/min in untreated controls) was associated with a 175% increase in PRA and a significant suppression of plasma irAng II (8.4±0.4 vs. 23±1.8 pg/ml in control animals; p is less than 0.005).

To evaluate the significance of the high ACE activity in monoamine-containing regions of dog brainstem, the metabolism of labelled Ang I and Ang II was measured. FIGS. 2A–2D show the results obtained in punches from the A2 region at the level of the obex. Hydrolysis of radio-labelled Ang I was evidenced by the rapid metabolism of the decapeptide into Ang-(1-8) and progressive accumulation of the N-terminal fragment Ang-(1-7). Only trace amounts of other hydrolytic products, including heptapeptide Ang-(2-8), were identified. Similar patterns of Ang I hydrolysis were obtained in other ACE-enriched regions of the brainstem, including the A1 (+10 mm), A5 (+14 mm), and A6 (+20 mm) regions. In the presence of 50 μM MK 422 the generation of Ang-(1-8), but not Ang-(1-7), was reduced to undetectable amounts (see FIGS. 3A and 3B). Experiments in which $^{125}$I-Ang II was incubated with brain punch homogenates revealed that Ang-(1-7) was the primary metabolic product.

DISCUSSION

High ACE-specific activity was found in the monoamine-containing regions of the brainstem and in the intermediolateral column of the spinal cord. The study further indicated that Ang-(1-7) is processed from Ang I in amounts equal to or greater than Ang II. In brainstem homogenates $^{125}$I-Ang I was metabolized to angiotensin II [Ang-(1-8)] and the N-terminal heptapeptide Ang-(1-7. In addition, the study demonstrated that Ang-(1-7) generation is not dependent upon Ang I converting enzyme (ACE) activity. In the presence of MK 422 (50 μM), an inhibitor of ACE, Ang-(1-7) was still generated, while the production of Ang-(1-8) was inhibited. It was surprising that the primary 125I-labelled peptide generated from either Ang I or Ang II was the N-terminal heptapeptide Ang-(1-7). Only trace amounts of C-terminal fragments including angiotensin (2-8) (i.e. Ang III) were observed. Although recently Tonnaer reported evidence for Ang-(1-7) generation in a rat synaptosomal fraction from whole brain (Tonnaier, J. A., Engles, G. M. H., Grant, W. E., Burbach, J. P., de Jong, W., DeWeid, D., *Protealytic conversion of angiotensin in rat brain tissue*. Eur. J. Biochem. 1983; 131: 415–421), the primary products of Ang I and Ang II were C-terminal fragments and not the N-terminal heptapeptide found in the present investigation. This study revealed the presence of high ACE activity in monoamine regions of dog brainstem and spinal cord, and showed that the metabolite Ang-(1-7) is the major product generated from Ang I in the presence and absence of ACE inhibition.

EXAMPLE 2

Evidence that the N-terminal heptapeptide Ang-(1-7) is a biologically active component of the renin-angiotensin system (RAS)

Since Ang-(1-7) was demonstrated to be a principle metabolite from Ang I which could be generated even in the presence of the angiotensin-converting enzyme (ACE) inhibitor MK-422, the results suggested that a direct pathway existed in the brain for the endogenous generation of Ang-(1-7). Although Ang-(1-7) had been previously shown to be an inactive component of the peripheral RAS, i.e. studies had indicated that Ang-(1-7) has no myotropic action on the rat colon in vitro [Regoli, D., and Vans, J. R., Br. J. Pharmacol., 23, 351–359, 1964], displays little or no pressure effect upon intravenous injection [Page, I. H., and Bumpus, F. M., Physiol. Rev., 41, 331–390, 1961], and may not act as a dipsogen [Tonnaer, J. A., Engels, G. M., Wiegant, V. M., Burbach, J. P., DeJong, W., and DeWeld, D., Eur. J. Biochem. 131, 415–421 1983], the consistent production of Ang-(1-7) from both Ang I and Ang II resulted in the investigation of the potential action of Ang-(1-7) as a central secretagogue.

Materials and Methods

Animals

Hypothalamo-neurohypophysial system (HNS) explants were prepared from 115 male Sprague-Dawley rats (275±5 g), 6–12 weeks old, as described by Sladek, et al. (Sladek, C. D. and Knigge, K. M., Endocrinology, 101, 411–420, 1977). The HNS explants, with the adenohypophysis removed, were 1 mm thick and extended from the median eminence to the preoptic area. In each experiment, five HNS explants were placed in a chamber (1 ml/vol) and perfused at 37° C. with Krebs solution (0.5 ml/min). The chamber was fashioned from a 3-ml syringe (horizontally oriented), with the inflow tube entering through the plunger of the syringe and the outflow tube attached to a needle placed at the luerlock tip of the syringe. HNS explants were oxygenated by equilibration of the perfusion medium with a gas mixture of 95% $O_2$/5% $CO_2$, and by circulating a gentle stream of this mixture through the chamber above the surface of the medium.

Experiments

After dissection of the explant and a one hour equilibration period, the effluent of the perfusion chamber was collected for periods of 15 minutes. Basal release of AVP was evaluated for 30 minutes, and the secretory effects of either Ang II or Ang-(1-7) were tested during one period beginning 30, 90 and 150 minutes after the start of sample collection at concentrations of 0.04, 0.4, and 4 μM, respectively. Time-control studies, in which Ang-(1-7) or Ang II was not added to the perfusate, were also carried out. In other experiments, the release of AVP from HNS explants was evaluated during 2.5 hours of continuous infusion of the competitive Ang II antagonist (Sar$^1$, Thr$^8$) Ang II at a dose of 20 μM. The agonist sections of Ang-(1-7) and Ang II (4 μM) on AVP release were compared after two hours of [Sar$^1$, Thr$^8$] Ang II treatment.

Extraction and Assay of AVP

The effluent obtained from the explants was assayed for AVP content after elution from a Bond-Elut phenyl-silica cartridge (Analytichem, Frampton, Calif.). The Bond-Elut cartridge was pretreated by sequential washes of 10 ml of 0.1% trifluoroacetic acid in 60% methanol and 10 ml of 0.1% trifluoroacetic acid in water. The Bond-Elut cartridge was then attached to the outflow port of the perfusion system and replaced with a fresh cartridge every 15 minutes. At the end of each 15 minute collection period, the Bond-Elut column was washed with 10 ml of $H_2$) and 10 ml of 0.1% trifluoroacetic acid in $H_2O$. AVP was eluted from the Bond-Elut with 5 ml of 0.1% trifluoroacetic acid in 60% methanol. The eluate was divided into two 2-ml aliquots and one 1-ml aliquot; eluates were evaporated on a rotary evaporator (Savant), and all three aliquots of each sample were assayed for AVP content. For RIA determinations of AVP, the residue was dissolved in 200 μl of 0.9% NaCl/0.1% bovine serum albumin/0.3% $CH_3COOH$. The minimum detection limit of the RIA (Arnel Products, N.Y.) was 0.5 pg. On average, recovery of $^{125}$I-labelled AVP from the Bond-Elut column was 89%. Values from RIA measurements were calculated as pg per 5 explants per 15 minutes.

Peptides

Ang II (Asp-Arg-Val-Tyr-Ile-His-Pro-Phe), Ang-(1-7) (Asp-Arg-Val-Tyr-Ile-His-Pro), and [Sar$^1$, Thr$^8$] Ang II (Sar-Arg-Val-Tyr-Ile-His-Pro-Thr) were synthesized. Peptides, prepared by solid phase peptide synthesis, were homogeneous by thin-layer chromatography (using three buffers of different pH), as well as by electrophoresis at pH 2.0. Amino acid analysis, after acid hydrolysis, indicated a correct ratio of amino acids for each peptide. The purity and relative concentrations of Ang II and Ang-(1-7) were confirmed by high performance liquid chromatography with a gradient-elution procedure as described by Chappell, et al. (Chappell, M. C., Brosnihan, K. B., Welches, W. R., and Ferrario, C. M., Peptides 8, 939–942, 1987).

Statistics

All values were expressed as means±SEM. Effects of Ang II and Ang-(1-7) in normal Krebs medium were compared by two-way analysis of variance and non-paired Student's t test; each response was compared with its immediately preceding control by Student's t test. Effects of [Sar$^1$,Thr$^8$] Ang II were evaluated by one-way analysis of variance. A P value of less than 0.05 was considered significant.

Results

Mean basal release of AVP during the control period averaged 199±53 pg in HNS explants exposed to Ang II and 177±43 pg in those treated with Ang-(1-7) (P is greater than 0.05). FIG. 4 shows that both Ang II and Ang-(1-7) produced concentration-related increases of AVP content in the HNS effluent, which, at the highest concentration tested (4.0 µM), amounted to 268% ±66% of control for Ang II and 216%±45% of control for Ang-(1-7). The increases in AVP release produced by Ang II or Ang-(1-7) at the highest concentration were of similar magnitude (P is greater than 0.05). In separate time-control experiments (n=5), the basal release of AVP from HNS explants was 281±47 pg. During the three time periods paralleling the application of the stimulus, there were minimal changes in the content of AVP in the effluent, averaging 107%±17%, 106%±10%, and 109%±18% of control values. Two-way analysis of variance showed that the differences between changes in AVP secretion obtained during time-control experiments and those obtained during the application of either Ang II or Ang-(1-7) were statistically significant (P is less than 0.05). In addition, comparison by two-way analysis of variance of the dose-related effects of Ang II and Ang-(1-7) on AVP release showed that the two peptides were equipotent with the range of concentrations tested in these experiments.

To evaluate the interaction of Ang-(1-7) and Ang II with [Sar$^1$, Thr$^8$] Ang II, additional HNS preparations were perfused with [Sar$^1$, Thr$^8$] Ang II (20 µM) for 2.5 hours, and Ang-(1-7 ) or Ang II (4 µM) was added during the penultimate 15 minute perfusion period, FIG. 5 illustrates the effect of [Sar$^1$, Thr$^8$] Ang II before and during the concomitant addition of either Ang-(1-7) or Ang II. For each set of experiments, the data are shown as a percentage of the average AVP release during the two periods preceding the addition of [Sar$^1$, Thr$^8$] Ang II. In the experiments in which Ang-(1-7) was added (n=4), basal AVP release averaged 131±39 pg. During the first 15 minutes of [Sar$^1$, Thr$^8$] Ang II treatment, AVP concentration in the effluent increased to 195%±24% over control values and remained elevated throughout the next two hour perfusion with [Sar$^1$, Thr$^8$] Ang II. Addition of Ang-(1-7) after two hours of [Sar$^1$, Thr$^8$] Ang II treatment caused no further increase in AVP release. For experiments in which Ang II was added in the presence of [Sar$^1$, Thr$^8$] Ang II (n=4), basal release of AVP was 105±11 pg, and during the first 15 minutes of [Sar$^1$, Thr$^8$] Ang II treatment AVP release increased to 185%±32% of control. Again, AVP release did not return to base line during the next two hours of [Sar$^1$, Thr$^8$] Ang II perfusion, and Ang II, like Ang-(1-7), did not cause further increases in the release of AVP. Compared with both Ang-(1-7) and Ang II, [Sar$^1$, Thr$^8$] Ang II was a relatively weak antagonist of AVP release from the HNS explant. Although both Ang-(1-7) and Ang II caused a significant increase in AVP release within 15 minutes of treatment, the five fold higher concentration of [Sar$^1$, Thr$^8$] Ang II produced an AVP release that was significantly increased above control values only after 30–45 minutes (see FIG. 5).

Discussion

The data presented above demonstrates that Ang-(1-7) is capable of stimulating the neurosecretory activity of AVP-containing cells in the rat HNS, in a dose-related manner and with a potency similar to that displayed by Ang II. In addition, the data indicates that neither Ang II nor Ang-(1-7) caused further enhancement of AVP release in the presence of the competitive Ang II antagonist [Sar$^1$, Thr$^8$]. As a result of these findings, the data suggests that a hydrophobic residue in position 8 of the angiotensin peptide is not essential for activation of angiotensin receptors. Moreover, the equipotence of Ang II and Ang-(1-7) indicates that Ang-(1-7) participates in the control of AVP release. Hence, in spite of negligible peripheral vascular agonistic activity and aldosterone-releasing effects, the data indicates that the Ang-(1-7) heptapeptide produces biological effects in the brain that are similar to those of Ang II.

EXAMPLE 3

Immunocytochemical localization of Ang-(1-7) in the brain

In order to understand the biological role of Ang-(1-7) in hypothalamic function, an antibody to Ang-(1-7) was developed and immunocytochemical studies were conducted to demonstrate the presence of this peptide in the rat hypothalamus.

Materials and Method

Animals

Twenty-four male Sprague-Dawley rats (200–250 g) were used in the study. Four of the rats received an injection of 1% colchicine (10 µl ) into a lateral cerebral ventricle, 36 hours period to perfusion. The animals received an overdose of sodium pentobarbital (200 mg/kg, i.p.) and were perfused transcardially with 0.9% NaCl and ice-cold picric acid-paraformaldenhyde-glutaraldehyde fixative. Frozen brain tissue was cut in the coronal plane at 30 µm on a sliding microtome. Tissue sections were collected into trays containing potassium phosphate buffered saline (PBS, 0.02M, pH 7.4) and then rinsed in this buffer.

Immunocytochemical procedure

Adjacent tissue sections were processed for immunocytochemical localization of Ang-(1-7), Ang II, or VP using the procedure described by Block and Hoffman (Block, C. H., and Hoffman, G. E., *Neuropeptide and Monoamine Components of the Parabrachial Pontine Complex*, Peptides 8, 267–283; 1987). The primary antisera were used at a dilution of 1:1000 in PBS/0.3% Triton X-100 (Tx). After a 48-hour incubation period in the primary antiserum at 4° C., tissue sections were rinsed thoroughly in PBS/0.3% Tx and incubated in goat anti-rabbit gamma globulin conjugated with fluorescein isothicyanate (FITC, 1:200 in PBS/0.3% Tx; Cappel Labs., PA) for one hour at room temperature. The reaction was stopped in 0.9% NaCl and tissue sections were mounted onto chrome-alum coated slides, air dried, and coverslipped with glycerol/PBS mounting media.

Antisera

Six polyclonal antisera directed against Ang-(1-7) were produced in rabbits using the antigen conjugated to keyhole limpet hemocyanin by glutaraldehyde. The antibodies specifically recognized Ang-(1-7) and Ang-(2-7). When Ang I, Ang II, Ang III [Ang-(2-8)], Ang-(1-4), VP, neurotensin, or substance P were fixed to filter paper with paraformaldehyde vapors and stained immunocytochemically, no cross-reactivity with the antiserum was observed. Tissue specificity of the antisera was further confirmed by the ability of 10 $\mu$g of purified Ang-(1-7), but not the other peptides, to completely block the staining of fibers and cells in the PVN and supraoptic nucleus as well as throughout the forebrain. Thus, the term "peptide-like"-ir is implicit to these results. Although each of the antiserum produced similar immunoreactive staining patterns in rat brain, the data in this example was obtained with one of the six antibodies. The primary antiserum to Ang II (Denise) was provided by Dr. D. Ganten (Heidelberg, FRG), while the VP antibody was obtained from INCSTAR Corp. (Stillwater, Minn.).

Analysis

Tissue sections taken through the forebrain and brainstem were examined for immunoreactive staining of fibers and cells using a microscopic (Microphot; Nikon, Inc., Garden City, N.Y.) equipped with epifluorescence illumination, 450–490 nm excitation filters and 510 nm dichroic mirror, for the detection of the FITC. An additional series of sections was counterstained with cresyl violet to reveal cytoarchitectural details of the structures under investigation. The atlas of Paxinos and Watson (Paxinos, G., and Watson, C., *The Rat Brain in Stereotactic Coordinates*, Sidney, Academic Press, 1986) was employed to define structures in the rat brain.

Results

Immunoreactive staining for Ang-(1-7) was found only in restricted areas of the rat forebrain. In contrast, VP and Ang II-ir were observed throughout the rat CNS. Since most of the Ang-(1-7)-ir was localized to the hypothalamus, staining patterns are documented in relation to the rostrocaudal subdivisions of PVN.

When the hypothalamic tissue was examined microscopically, immunoreactive Ang-(1-7) was observed within the cells of the magnocellular paraventricular hypothalamic and supraoptic nuclei. Fibers from the paraventricular region were observed to course ventrally toward the supraoptic nucleus in a manner similar to vasopressin projections. Many immunoreactive Ang-(1-7) fibers were also observed in the internal zone of the median eminence (a region containing fibers that terminate on capillaries of the hypophysial-portal system) and throughout the retrochiasmatic region. Although this pattern of immunoreactivity was similar to that of Ang II, the intensity of the fluorescence for Ang-(1-7) was much more pronounced. In the central nucleus of the amygdala, a region known to contain dense plexuses of Ang II fibers, there was no detectable Ang-(1-7) immunoreactivity. Additionally, pre-incubation of the antiserum with Ang I, Ang II or vasopressin antigens did not block the staining pattern.

The striking pattern of Ang-(1-7) immunoreactivity in hypothalamic neurons and fibers of the median eminence, a region which projects primarily to the posterior lobe of the pituitary and the CNS regions participating in the central control of endocrine function, together with its recently discovered effect on vasopressin release, supports a role for this peptide within the hypothalamic neurosecretory system.

EXAMPLE 4

Evidence that both Ang II and Ang-(1-7) are equipotent in eliciting centrally mediated changes in blood pressure on the basis that the heptapeptide Ang-(1-7) was found to be (1) the major product formed by incubation of homogenates of dog brainstem with radiolabelled Ang I at a neutral pH; (2) generated both in the absence and presence of the angiotensin converting enzyme (ACE) inhibitor MK-422; and (3) in spite of its negligible peripheral properties, equipotent with Ang II in promoting release of AVP from the perfused explant of the rat hypothalamusneurohypophysial system (HNS), an investigation was undertaken to determine whether Ang-(1-7) had similar depressor effects as Ang II.

In this regard, the effects produced by the injection of 0.1 to 250 pmol Ang-(1-7) into the dorsomedial medulla (DMM) on mean arterial pressure (MAP) and heart rate (HR) of chloralose-urethane anesthetized rats (240–280 g) was investigated. In the dorsomedial medulla oblongata (DMM) of the rat, dense concentrations of specific, high affinity Ang II binding sites exist in the nucleus tractus solitari (nTS) and dorsal motor nucleus of the vagus (dmnX), with lower concentrations in the area postrema (Brosnihan, K. B., D. I. Diz, M. T. Schiavone, D. A. Averill, and C. M. Ferrario, *Approaches to Establishing Angiotensin II as a Neurotransmitter, In Brain Peptides and Catecholamines in Cardiovascular Regulation*, edited by J. P. Buckley and C. M. Ferrario, New York, N.Y.; Raven Press, pp. 313–328, 1987; and, Ferrario, C. M., Barnes, K. L., Diz, D. I., Block, C. H., and Averill, D. B., *Role of the Area Postrema Pressor Mechanisms in the Regulation of Arterial Pressure*, Can. J. Physiol. Pharmacol. 65: 1591–1597, 1987). Studies by the present inventors showed that the DMM region may be a major site at which afferent inputs from baroreceptors are exposed to neuromodulation by Ang II (Campagnole-Santos, M. J., Diz, D. I., and Ferrario, C. M., *Baroreceptor Reflex Moduation by. Angiotensin II at the Nucleus Tractus Solitarii*, Hypertension 11 (Suppl. I): I-167-I-171, 1988). The observations that Ang III [Ang-(2-8)] elicits potent centrally mediated cardiovascular and dipsogenic responses (Hardin, J. W., and Felix, D., *Angiotensin Sensitive Neurons in the Rat Paraventricular Nucleus: Relative Potencies of Angiotensin II and Angiotensin III*, Brain Res. 410: 130–134, 1987; and, Wright J. W., Morset, S. L., Abhold, R. H., and Harding, J. W., *Pressor Action and Dipsogenicity Induced by Angiotensin II and III in Rats*, Am. J. Physiol. 249: R514–R521, 1985) raised a question as to whether the neuronal actions of Ang II may be conveyed, at least in part, by shorter sequences of Ang peptides.

Further evidence for the possibility that shorter sequences of Ang peptides produce the same neuronal actions of Ang II was provided by the unexpected demonstration (Examples 1 and 2 above) that Ang-(1-7), the amino terminal fragment of Ang II, is present in the brain and possesses significant central actions. Following the demonstration that Ang-(1-7) is generated directly from radiolabeled Ang I by brain punch homogenates (see Example 1), further studies (as set forth in Example 3 above) revealed that this fragment is contained in the perikarya and axonal processes of the supraoptic and paraventricular nuclei of the hypothalamus and represents a major Ang peptide as identified by HPLC elution profiles of the brain stem. With the discovery that Ang-(1-7) is as potent as Ang II in stimulating vasopressin release from neurohypophyseal explants (Example 2), other facets of Ang-(1-7) putative biological actions were investigated by deterring the site specific, dose-related, hemodynamic effects of Ang-(1-7) microinjected into the nTS and dmnX.

Methods and Materials

Experiments were performed in 63 male Sprague-Dewley rats, (Harlan-Sprague-Dawley, Indianapolis, Ind., USA), weighing between 240–280 g. After anesthesia with chlorase-urethane (35 mg/kg and 750 mg/kg, i.p. respectively), catheters were inserted into a femoral artery and vein. Arterial pressure was monitored with a solid state strain gauge transducer (Model MP-15D, Micron Instruments, Los Angeles, Calif., USA) while heart rate (HR) was determined with a cardiotachometer (Model 2000, Gould, Cleveland, Ohio, USA) triggered by the arterial pressure wave. All variables were displayed on a direct-writing Gould polygraph (Series 2400).

Rats were placed in a stereotaxic frame (David Kopf Instruments, Tujunga, Calif., USA) with their heads flexed downward at 45 degrees. The dorsal surface of the medulla oblongata was exposed by incising the atlanto-occipital membrane. Unilateral microinjections of 100 nl of Ang II, Ang-(1-7), and artificial cerebrospinal fluid (aCSF) were made with a multi-barreled glass micropipette (30–50 $\mu$m outer diameter). Ang II and Ang-(1-7), synthesized by Dr. M. C. Khosla (The Cleveland Clinic Foundation, Cleveland, Ohio), were dissolved in aCSF. Solutions were given over one minute after positioning the pipette either into the nTS (0.5 mm rostral and 0.5 mm lateral to obex; 0.3 mm below the dorsal surface) or into the dmnX (0.5 mm rostral and 0.5 lateral to the obex; 0.5–0.6 mm below the dorsal surface). In 45 rats the cardiovascular effects of microinjection of low doses (0.1, 0.5, 2.5, and 12.5 ng) of Ang-(1-7) into either the nTS (n=31) or the dmnX (n=14) were measured. In 22 of the above rats, the effect of low doses of Ang II (0.1, 2.5 ng) was also evaluated (nTS, n=12; dmnX, n=10). In an additional 18 rats, the actions of the Ang peptides given at a much larger dose (250 ng) were determined. Injections of test substances were randomized, and a minimum of 30 min. was allowed between injections. In some animals, injections were made in both sides of the brain stem; however, only one nucleus was investigated per side. At the completion of all experiments, the location of the pipette's tip was marked by injecting 50 nl of a 2% solution of Alcian blue dye from one barrel of the pipette. The deposition of the dye within the structures of the DMM was examined in 50 $\mu$m serial sections stained with thionine.

Kruskal-Wallis non-parametric tests were used to evaluate differences between responses to vehicle injections (aCSF) and the Ang peptides. Differences between Ang II and Ang-(1-7) were analyzed bSF Signed Rank Tests (Zara, J. H., *Biostatistical Analyses*, Englewood Cliffs, N.J.; Prentice-Hall, Inc., 1974). The criterion for statistical significance was set at P less than 0.05. Numerical values are given as means ±SEM.

Results

The baseline mean arterial pressure (MAP) and HR of 63 rats anesthetized with chloralose-urethane average 94±1 mm Hg and 351±4 beats/min, respectively. The individual MAP and HR responses were obtained with unilateral microinjections of Ang-(1-7) into the medial aspect of the nTS (n=31) are shown in FIG. 6. Ang-(1-7) caused significant reductions in MAP averaging −7±1 mm HG and −10±2 mm HG at doses of 0.1 and 12.5 ng, respectively. The hypotension was accompanied by significant decreases in HR, which averaged −6±1 beats/min, and −10±2 beats/min at the above two doses, respectively (FIG. 6). When the effects of both Ang II and Ang-(1-7) were determined in the same animals, it was observed that microinjection of 0.1 ng Ang II into the nTS (n=5) produced a decrease in MAP (−16±3 mm Hg) which was significantly greater than that obtained with 0.1 ng of Ang-(1-7) (−9±1 mm Hg; P less than 0.05). However, at a dose of 2.5 ng, Ang II and Ang-(1-7) elicited similar decreases in MAP (−18±2 mm Hg and −15±2 mm Hg, respectively; n=7). The bradycardia produced by injections of Ang II and Ang-(1-7) into the nTS were similar −13±3 versus −9±2 beats/min at 0.1 ng and −14±4 versus −10±3 beats/min at 2.5 ng. Time-dependent components of the nTS-mediated effects of Ang-(1-7) and Ang II on MAP and HR are shown in Table 1 below.

TABLE 1

Time Parameters of the Hemodynamic Effects of two Angiotensin Peptides In the nTS

| Dose (ng) | HEART RATE | | | MEAN BLOOD PRESSURE | | |
|---|---|---|---|---|---|---|
| | Onset | Peak (seconds) | Duration | Onset | Peak (seconds) | Duration |
| Ang-(1-7): | | | | | | |
| 0.1 | 26 ± 8* | 62 ± 16 | 188 ± 32* | 39 ± 16 | 39 ± 3 | 159 ± 3 |
| 2.5 | 44 ± 16* | 88 ± 21 | 328 ± 58 | 23 ± 7 | 97 ± 21* | 361 ± 58* |
| Ang-II: | | | | | | |
| 0.1 | 60 ± 14# | 116 ± 24# | 442 ± 74# | 28 ± 4 | 40 ± 10 | 206 ± 51 |

TABLE 1-continued

Time Parameters of the Hemodynamic
Effects of two Angiotensin Peptides In the nTS

| Dose (ng) | HEART RATE | | | MEAN BLOOD PRESSURE | | |
|---|---|---|---|---|---|---|
| | Onset | Peak (seconds) | Duration | Onset | Peak (seconds) | Duration |
| 2.5 | 81 ± 17# | 68 ± 21 | 342 ± 50 | 20 ± 8 | 45 ± 8 | 224 ± 20 |

Values are means ± SE. Values for peak and duration are calculated from the onset.
(*) = P < 0.05 compared to Ang II
(#) = P < 0.05 for differences of the same time parameter between the heart rate and mean blood pressure Although the time to peak fall in HR was not different for the two Ang peptides, the onset of the HR response was significantly delayed for Ang II as compared with Ang-(1-7) at both doses (Table 1). No differences for the onset of the MAP response were observed between the two peptides.

Unilateral microinjections of Ang-(1-7) into the dmnX (FIG. 7) elicited hypotensive and bradycardic responses similar in both magnitude and duration to those produced by injection of the peptide in the nTS. In addition, the decreases in MAP and HR produced by Ang-(1-7) were not different from those produced by the administration in the same animals of Ang II. At a low dose of 0.1 ng, injection of Ang-(1-7) into the dmnX decreased MAP by −8±2 mm Hg and HR by −16±4 beats/min. In the same animals, 0.1 ng of Ang II decreased MAP and HR by −14±3 mm lg and −19±3 beats/min, respectively. Injection of 2.5 ng of Ang II produced a decrease in MAP (−14±2 mm Hg) of a magnitude not different than that obtained with the lower dose, or with 2.5 ng of Ang-(1-7) (−13±2 mm Hg). The fall in HR produced by injection of 2.5 ng of Ang II (−6±2 beats/min; P less than 0.05) was smaller than that obtained with the lower dose. The HR response to 2.5 ng of Ang-(1-7) was −8±2 beats/min; not different from that obtained with Ang II (−6±2 beats/min). No significant differences were observed in the time-related components of the cardiovascular response to injections of either Ang-(1-7) or Ang II in the dmnX (Table 2 below). However, there was a similar tendency for the onset of the HR response induced by Ang II to occur later than that for the MAP response as was observed in the nTS.

by the present inventors have documented that diffusion of the injectate, as determined by assessing spread of $^{125}$I-radiolabeled Ang II using this microinjection technique, is confined to the nucleus of interest (Campagnole-Santos, et al. supra).

Discussion

Unilateral microinjections of Ang-(1-7) into the medial nucleus tractus solitarii caused depressor effects at doses between 0.1 and 12.5 ng. Hypotension was accompanied by bradycardia. Similar hypotensive responses associated with bradycardia were produced by injections of Ang-(1-7) into the dorsal motor nucleus of the vagus. The magnitudes of the monophasic depressor responses were comparable to those obtained using similar doses of Ang II in both nuclei. Injection of higher doses of Ang-(1-7) or Ang II caused variable biphasic depressor/pressor responses. Evidence is thus provided for neurally mediated responses to an Ang II fragment known to be devoid of agohist actions on blood vessels. These new findings suggest marked differences in the receptor requirements for vascular and nervous tissue. The results also support the concept of tissue specific formation and action of angiotensin peptides in brain regions involved in the reflex control of arterial pressure and heart rate.

The above results extended the original observations of site and dose specific hemodynamic effects of Ang II injections in the medulla oblongata of the rat (Diz, D. I., Barnes, K. L., and Ferrario, C. M., *Hypotensive Actions of Microinjections of Angiotensin II into the Dorsal Motor Nucleus of the Vagus*, J. Hypertens. 2: 53–56, 1984) by demonstrating that the N-terminal heptapeptide Ang-

TABLE 2

Time Parameters of the Hemodynamic
Effects of two Angiotensin Peptides in the dmnX

| Dose (ng) | HEART RATE | | | MEAN BLOOD PRESSURE | | |
|---|---|---|---|---|---|---|
| | Onset | Peak (seconds) | Duration | Onset | Peak (seconds) | Duration |
| Ang-(1-7): | | | | | | |
| 0.1 | 56 ± 20 | 114 ± 47 | 430 ± 115 | 29 ± 10 | 63 ± 28 | 306 ± 112 |
| 2.5 | 49 ± 21 | 49 ± 14 | 368 ± 16 | 24 ± 12 | 69 ± 33 | 257 ± 55 |
| Ang-II: | | | | | | |
| 0.1 | 83 ± 20 | 136 ± 36 | 482 ± 153 | 20 ± 6 | 39 ± 8 | 310 ± 78 |
| 2.5 | 81 ± 41 | 63 ± 23 | 288 ± 75 | 12 ± 7 | 37 ± 9 | 207 ± 25 |

Values are means ± SE. Values for peak and duration are calculated from the onset.

In additional experiments (n=18), the effects of injecting Ang-(1-7) and Ang II at a dose of 250 ng were compared. At this high dose, Ang-(1-7) and Ang II frequently had either a biphasic depressor/pressor action on MAP or produced a pure pressor response accompanied by variable changes in HR.

Microscopic examination of the brain stem was employed to verify the accuracy of the pipette tip placement after every experiment. The data presented above represent only those experiments where injections were confined to either the nTS or dmnX. Previous studies (1-7) also elicits actions essentially similar to those produced by the octapeptide Ang II.

This is a significant finding because it has been concluded from other studies that fragments of Ang II lacking an amino acid residue in the eighth position are biologically inert. Although C-terminal fragments of Ang II such as Ang-(2-8) (Ang III) produce potent central agonistic properties, the biological response appeared to remain dependent on phenylalanine (Phe)

in the ultimate amino acid position of Ang II. Thus, investigators have had no prior reason to suspect that the actions of Ang II in the central nervous system may be expressed, either fully or in part, by end products of the RAS lacking the phenyl group in position 8. The data presented above suggests that receptors in the brain stem can interact with Ang congeners containing proline in the last (7th) position of the molecule. By inference, these receptors, unlike those in peripheral vascular tissue, do not show an absolute requirement for Phe in the 8th position. This interpretation is in agreement with the recent demonstration set forth in Example 1 above that Ang-(1-7) is as potent as Ang II in stimulating the release of vasopressin in isolated explants of the rat's hypothalamus. Although it remains to be explored whether the actions of Ang-(1-7) are mediated by the same receptor system identified for Ang II, the studies indicate that N-terminal fragments of Ang II are potent agonist products of the RAS in the brain.

Ang-(1-7) at doses between 0.1 and 12.5 ng elicited small, but statistically significant, depressor effects on blood pressure and HR whether injected into either the nTS or the dmnX. On average the depressor effect began within 29 seconds while the maximal fall in MAP was recorded within 2 minutes after delivery of the heptapeptide. The falls in MAP and HR were relatively short lasting with the variables returning to baseline within 5-6 min. Neither the dose nor the site at which Ang-(1-7) was injected had a marked influence on the time-dependent characteristics of the monophasic depressor responses. However, when very large doses (250 ng) of Ang-(1-7) were given into either the nTS or the dmnX, the decreases in MAP converted to either biphasic depressor/pressor or pure pressor effects which were associated with variable changes in HR. These findings confirmed previous observations by the present inventors of dose-dependent actions of Ang II in the nTS and the dmnX.

In earlier studies of the cardiovascular effects of microinjection of Ang II in the nTS or the dmnX, it was not possible to exclude entirely whether a part of the centrally mediated hypotensive actions of the peptide was masked by leakage of Ang II into the systemic circulation. Because Ang-(1-7) is devoid of agonistic actions on blood vessels and has no direct pressor activity when injected into a vein (Page, I. H., *Polypeptide Hormone Receptors and Conformation of Angiotensin. In: Hypertension Mechanisms*, Orlando, N.Y.: Grune and Stratton, Inc., pp. 355-370, 1987), the present inventors conclude that the hemodynamic effects of Ang-(1-7) are due to an action of the heptapeptide on receptors modulating the activity of cardiovascular neurons.

In agreement with previous studies by the present inventors, the results confirmed that Ang II elicits depressor effects when given into structures of the DMM in small doses (less than 3 ng). Moreover, the effects of Ang II were found to be comparable in magnitude and direction to those obtained by injection of Ang-(1-7) at these sites. Comparison of the time-dependent components of the monophasic depressor responses produced by nTS injections of Ang-(1-7) and Ang II showed a consistent and significant difference in the onset time of the bradycardia at both doses tested. While Ang-(1-7) caused relatively rapid and parallel falls in MAP and HR, a different pattern was observed for injections of Ang II into the nTS. The onset of the Ang II mediated bradycardia was significantly delayed with respect to the accompanying fall in MAP. The asynchrony between the onset of the falls in MAP and HR was observed with Ang II in the nTS, with a similar tendency in the adjacent dmnX. Thus, these findings suggest that the agonistic effects of Ang II on receptors influence the cardiac rate required for processing of the octapeptide to Ang-(1-7).

On the basis of the above results, it can be concluded that receptors mediating angiotensin responses in the brain, unlike those in the peripheral circulatory system, do not have an absolute requirement for the presence of an amino acid in the 8th position. Furthermore, the data obtained above is also compatible with the present inventors' findings that N-terminal fragments of Ang II are produced endogenously in the brain and that Ang-(1-7) accounts for some of the varied central actions previously ascribed to Ang II.

EXAMPLE 5

Evidence that Prolylendopeptidase is responsible for for the generation of Ang-(1-7) from Ang I and/or Ang II and that Z-Pro-prolinal (ZPP) is an effective inhibitor specific for Ang-(1-7) formation It has long been evident that there are many enzyme pathways for the processing and metabolism of angiotensin neuropeptides. While ACE plays a crucial role in the processing of Ang I to Ang II, other endo- and carboxypeptides contribute as well. The observation that Ang-(1-7) was produced from labelled Ang I after ACE inhibition by MK 422 demonstrated the existence of an alternative pathway for the generation of this heptapeptide.

Prior to the present investigation, little was known of the neuroenzymes and putative metabolic pathways which are involved in the production of Ang-(1-7) from either Ang I or Ang II. In theory, there are a number of enzymes which could have been responsible for the production of the N-terminal heptapeptide Ang-(1-7). In this regard, the potential candidates included: prolyl endopeptidase (E.C. 3.4.21.26) which has been found to be involved in the metabolism of a number of neuropeptides such as thyrotropin releasing hormone (TRH), luteinizing hormone releasing hormone (TRH), Angiotensin II, bradykinin, substance P, and neurotensin [(Andrews, P., Hines, C., and Dixon, J., *Characterization of Proline Endopeptidase from Rat Brain*, Biochem. 19: 5494-5500, 1980); (Orlowski, M., Wilk, E., Pearce, S., and Wilk S., *Purification and Properties of a Prolyl Endopeptidase from Rabbit Brain*, J. Neurochem. 33: 461-469, 1979); (Orlowski, M., and Wilk, S.: *Purification and Specificity of a Membrane-Bound Metalloendopeptidase from Bovine Pituitaries*, Biochemistry, 20: 4942-4950, 1981); and, (Greene, L. J., Spadaro, A. C. C., Martins, A. R., Perussi de Jesus, W. D., and Camargo, A. C. M.; *Brain Endooliopeptidase B: A Post-Proline Cleaving Enzyme that Inactivates Angiotensin I and II*, Hypertension 4: 178-184, 1982)], enkephalinase (neutral endopeptidase 24.11) [(Sullivan, S., Akil, H., and Barchas, J. D.; *In Vivo Degradation of Enkephalin: Evidence for Cleavage at the Gly-Phe bond*, commun. Psychopharmacol. 2: 525, 1978); and, (Skidgel, R. A., Engelbrecht, S., Johnson, A. R., and Erdos, E. G.; *Hydrolysis of Substance P and Neurotensin by Converting Enzyme and Neutral Endopeptidase*, Peptides 5: 769-776, 1984)] and membrane-bound proline endopeptidase (Checler, F., Amar, F., Kitabgi, P., and Vincent, J.; *Metabolism of Neurotensin by Neutral N(N-Neuroblastoma NIE 115) and Extraneural (HT 29) Cell Lines*, Peptides 7: 1071-1077, 1986). Of the potential enzymes, the following studies demonstrate that prolyl endopeptidase is the enzyme responsible for the production of Ang-(1-7). In addition, the studies indicate that a specific inhibitor of prolyl endopeptidase, i.e. Z-Pro-prolinal prevents the formation of Ang-(1-7) from Ang I and/or Ang II.

The studies set forth above demonstrated that in canine brainstem homogenates, Ang-(1-7) is the principal metabolite of Ang I and that Ang-(1-7) also resembles Ang II in its capacity to release vasopressin in the hypothalamoneurohypophseal explant. As a result of these discoveries, the enzyme(s) involved in the production of Ang-(1-7) in homogenates (20 mM TRIS HCl buffer, pH 7.5) of dog hypothalamus were evaluated. After centrifugation (10,000 g×10 min) aliquots of the supernatant were added to an assay solution containing the same buffer, 0.01% BSA and 30 pM $^{125}$I-Ang I. The production of $^{125}$I-Ang-(1-7) was determined by HPLC as set forth in Example 1 above. Incubation in the presence of Z-Pro-prolinal (ZPP), an inhibitor specific for prolylendopeptidase, decreased the rate of Ang-(1-7) production by 90%. Additions of the thiol reagent DTT (1 mM), an activator of prolylendopeptidase, increased the rate of generation of Ang-(1-7) about three fold and under these conditions the inclusion of ZPP (1 µM) produced a 98% inhibition of the Ang-(1-7) production. Phosphoramidon (an inhibitor specific for enkephalinase) caused a 12% inhibition of Ang-(1-7) formation and EDTA (a general metalloproteinase inhibitor) caused a 41% increase in Ang-(1-7) formation. Partial purification of the prolylendopeptidase from homogenates of the dog's hypothalamus by chromatography on a Sephacryl S-300 column gave a single peak of prolylendopeptidase-like activity using as substrate N-succinylglycyl-L-proline 7-amido-4 methylcoumarin. The pI of the canine enzyme, determined by a chromatofocusing column, was 4.8, consistent with values in other species. These results demonstrate that prolylendopeptidase is involved in the formation of Ang-(1-7) in hypothalamic homogenates and excludes the major involvement of other soluble endopeptidases.

In addition, the above results demonstrate that Z-Proprolinal (ZPP) is a specific inhibitor for Ang-(1-7) formation in the renin-angiotensin system (RAS). This discovery in combination with Drs. Wilk and Orlowski's findings that Z-Pro-prolinal (ZPP) readily traverses the blood-brain barrier (BBB) (Orlowski, supra, and Orlowski, and Wilk, supra) in mammals indicates that Z-Pro-prolinal can be an effective pharmaceutical agent for the treatment of hypertension in mammals.

EXAMPLE 6

Evidence that the administration of an effective amount of Z-Pro-prolinal (ZPP) inhibits Ang-(1-7) formation and lowers blood pressure In order to assess the effectiveness of Z-Proprolinal, the specific inhibitor of prolyl endopeptidase, in controlling blood pressure the following study was conducted. The third ventricle surrounding the hypothalamic region in 12 week old spontaneously hypertensive rats (SHR) (obtained from Taconic Farms, New York) was per±used via push-pull cannula with artificial control CSF (a C5F) or G5 im MK+ CSF (K-CSF) (20 µl/min) with or without Z-Pro-prolinal (Zpp 1 µM provided by Dr. Sherwin Wilk, Mount Sinai School of Medicine, New York, N.Y.) under anesthesia with Inacton. Similar studies were performed in age-matched normotensive Wistar-Kyoto control rats (WKY) (obtained from Taconic Farms, New York). The results of the studies are set forth in FIGS. 8-11.

In SHR (n=21), basal mean arterial pressure (MAP) was 156±5 mmHg, and perfusion with ZPP (n=13) caused a significant decrease in mean arterial pressure (−37±4 mmHg) (p is less than 0.05) (FIG. 8B) which was not accompanied with a significant change in heart rate (HR) (384±10 to 376±19 beats/min) (FIG. 9B). In WKY (n=13), ZPP had no effect on either MAP (FIG. 8A) or HR (99±6 to 100±7 mmHg, 379±18 to 368±27 beats/min) (FIG. 9A).

In SHR, administration of a depolarizing concentration of K+ caused a reduction in MAP (−19±4 mmHg) (FIG. 10B) and HR (−32±7 beats/min) (n=17) (FIG. 11B). Pretreatment with ZPP did not change the magnitude of the fall in MAP, in response to K+ but attenuated the HR response. In WKY, the reduction in MAP (−16±3 mmHg) (FIG. 10A) and HR (−37±7 beats/min,) (FIG. 11A) by K+ was attenuated by ZPP (−6±4 mmHg and −13±8 beats/min).

Thus, the results clearly indicate that the administration of an effective amount of Z-Pro-prolinal (ZPP) to hypertensive specimens causes a significant decrease in blood pressure without a notable change in heart rate, demonstrating that Z-Pro-prolinal (ZPP) is an effective agent for controlling hypertension in mammals.

EXAMPLE 7

Evidence that the Neutral Endopeptidase 3.4.24.11 Participates in the Conversion of Ang I to Anq-(1-7) and that SCH 39,370 is an Effective Inhibitor of Ang-(1-7) Formation The processing enzymes involved in the formation of circulating Ang-(1-7) following intravenous administration of angiotensin I (1-10) to conscious spontaneously hypertensive and Wistar Kyoto rats were further investigated. Immunoreactive products including angiotensin I, angiotensin II (i.e. Ang-(1-8)) and Ang-(1-7) were measured in arterial blood by three specific radioimmunoassay. Angiotensin I infusion (2 nmol) induced a rapid increase in immunoreactive angiotensin II and Ang(1-7). Pretreatment with the angiotensin converting enzyme inhibitor enalaprilat (MK-422, 2mg/kg) eliminated angiotensin II (1-8) formation and augmented circulating levels of angiotensin I and Ang-(1-7) in spontaneously hypertensive and Wistar Kyoto rats. The elevated levels of Ang-(1-7) in enalaprilat treated rats were blocked by concurrent treatment with the neutral endopeptidase 24.11 (NEP 3.4.24.11) inhibitor SCH 39,370 (N-{N-[1-(S)-carboxy-3-phenylpropyl]-(S)-phenylalanyl}-(S)-isoserine) at a dose of 15 mg/kg in both strains. Administration of SCH 39,370 alone decreased Ang-(1-7) levels in SHR, whereas angiotensin II levels increased in both strains (p <0.01). Comparisons of the metabolism of angiotensin I in the two rat strains showed increased formation of Ang-(1-7) in spontaneously hypertensive rats not given any of the enzyme inhibitors. In addition, levels of angiotensin I were higher after administration of SCH 39,370 in hypertensive rats. These novel findings reveal that neutral endopeptidase 24.11 participates in the conversion of angiotensin I to Ang-(1-7) and in the metabolism of angiotensin II in the circulation of both spontaneously hypertensive and Wistar Kyoto rats and that SCH 39,370 in an effective inhibitor for Ang-(1-7) formation.

Background

As indicated above, Ang-(1-7) is the first member of the angiotensin (Ang) peptide family to cause cells to secrete hormones and release autacoids without eliciting accompanying changes in blood pressure, water intake and aldosterone secretion. Incubation of hypothalamic explants with Ang-(1-7) stimulates a dose dependent release of vasopressin. Addition of Ang-(1-7) to human astrocytes and vascular endothelial cells promotes production of prostanoids by activation of a $Ca^{++}$ independent second messenger system. Ang I forms Ang-(1-7) in brain homogenates, vascular endothelium and neuronal cells in culture. These effects of Ang-(1-7) have prompted the inventors to suggest a regulatory role for this peptide as a paracrine hormone.

As shown above, inhibition of angiotensin converting enzyme (ACE) augments the concentration of Ang-(1-7) in plasma. This evidence suggests that alternate enzymatic pathways exist for the processing of biologically active Ang peptides. In searching for peptidases that hydrolyze the $Pro^7$-$Phe^8$ bond of Ang I or Ang II, the inventors have found that prolyl endopeptidase (E.C.3.4.21.26) is an Ang-(1-7) forming enzyme in neuroblastoma glioma cells and brain tissue. But inhibition of prolyl endopeptidase did not prevent the generation of Ang-(1-7) in other tissues. Therefore the inventors have now investigated whether neutral endopeptidase E.C.3.4.24.11 (NEP 24.11) is involved in the metabolism of Ang I into Ang-(1-7). Studies were done in conscious spontaneously hypertensive rats (SHR) and Wistar Kyoto (WKY) controls in which Ang I was injected intravenously (i.v.) in the absence and presence of specific inhibitors of ACE, prolyl endopeptidase and NEP 24.11.

Method and Materials

Experimental Protocol

All experiments were carried out in strict adherence to the principles sponsored by the American Physiological Society. Male 16-week-old SHR($319\pm4$ gm) and WKY($315\pm4$ gm) controls (Charles River, Wilmington, Mass.) were housed in rooms maintained on a 12 hr light-dark cycle. Animals ate a solid diet of rat chow (Purina, Bedford, Ohio) and had free access to water. Cannulas (PE-50 and PE-10, Clay Adams Becton Dickinson, Parsippany, N.J.) were implanted into a femoral artery and vein using aseptic conditions in rats anesthetized with 1% halothane 24 hours beforehand. The free ends of the cannulas were tunneled under the skin and externalized at the back of the neck.

Conscious rats were divided into five groups. Group I (n=4 SHR and 4 WKY) received an i.v. injection of 0.9% NaCl. Group II (n=4 SHR and 4 WKY) was given an i.v. injection of enalaprilat (MK-422,2 mg/kg). Group III (n=4 SHR and 4 WKY) was injected with (N-{N-[1-(S)-carboxy-3-phenylpropyl]-(S)-phenylalanyl}-(S)-isoserine) at a dose of 15 mg/kg. This compound (SCH 39,370) is a specific and potent inhibitor of NEP 24.11 but does not inhibit ACE or carboxypeptidase A (Sybertz EJ, Chiu PJS, Vemuiapalli S, Pitts B, Foster SJ, Barntt WA, Hashlanger MF: SCH 39370, *A Neutral Metalloendopeptidase Inhibitor, Potentiates Biological Responses to Atrial Natriuretic Factor and Lowers Blood Pressure in DOCA-Na Hypertensive Rats.* J. Pharmacol. Exp. Ther. 250:624–631,1989). Group IV (n=4 SHR and 4 WKY) received both MK-422 (2 mg/kg) and SCH 39,370 (15 mg/kg). Group V (n=3 SHR and 3 WKY) were given MK-422 (2 mg/kg) and Z-prolyl-prolinal (5 mg/kg), a specific inhibitor of prolyl endopeptidase (Friedman TC, Orlowski M, Wilk S: *Prolyl Endopeptidase: Inhibition in vivo by N-benzyloxycarbonyl-prolyl-prolinal.* J. Neurochem. 42:237–241,1984). Either saline (vehicle) or the enzyme inhibitors were administered 20 minutes before an i.v. injection of 0.2 ml of Ang I (2 nmol) in heparinized saline. Serial samples of arterial blood (0.2 ml) were rapidly collected into ice-chilled tubes containing 5 ml of 80% ethanol/0.1N HCL every 15–30 sec before and after injection of Ang I. The amount of blood removed in each sample was replaced with an equal volume of saline. The dead space (0.08 ml) of the femoral artery catheter was cleared of any remaining saline or blood before obtaining the samples.

Peptide Extraction and Analyses: Samples were centrifuged at 5,000 g for 20 minutes; the supernatant was stored for 12 hours at $-20°$ C. After a second centrifugation step (10,000 g, 20 min) the supernatant was diluted 1:1 (V:V) with 1% heptaflurobutyric acid (HFBA), stored for 4–6 % hours at 4° C., and centrifuged again at 15,000 g. This supernatant was further diluted 1:4 with 0.2% HFBA and concentrated on a Sep-Pak Vac Cartridge (Millipore Co., Milford, Mass.) activated beforehand with 3 ml of 60% acetonitrile/0.2% HFBA, 3 ml of 0.1% bovine serum albumin in 0.2% HFBA, and 5 ml of HFBA. After application of the supernatant, the column was washed with 10 ml of 0.2% HFBA. Angiotensin peptides were eluted with 8 ml of 60% acetonitrile/0.2% HFBA. Fractions were evaporated to dryness in a vacuum centrifuge (Savant Instrument Inc., Hicksville, N.Y.) for measurements by radioimmunoassay (RIA). Different aliquots of the samples were assayed to ensure linearity. Peptide recovery for Ang I added to the acid ethanol solution prior to blood sample averaged $85\pm4\%$, n=6, SFM): peptide values were not corrected for recovery. Moreover, no in vitro conversion of Ang I into either Ang-(1-7) or Ang II was observed.

The RIAs employed by the inventors to determine concentrations of Ang I, Ang II, and Ang-(1-7) are described in detail elsewhere. See, Chappell MC, Brosnihan KB, Diz DI, Ferrario CM: *Identification of Angiotensin-(1-7) in Rat Brain: Evidence for Differential Processing of Agiotensin Peptides.* J. Biol. Chem. 288:16518–16523,1989; and, Kohara K, Brosnihan KB, Chappell MC, Khosla MC, Ferrario CM: Angiotensin-(1-7): *A Member of Circulating Angiotensin Peptides.* Hypertension 17:131–138, 1991. The Ang I antibody (New England Nuclear, Boston, Mass.) shows a 100% cross-reactivity with Ang I, Ang-(2-10) and Ang-(3-10) but does not cross-react with either Ang II or Ang-(1-7). The sensitivity of the Ang I assay (defined as twice the minimum detection level) averaged 5 fmol/tube. The Ang II antibody was produced by the inventors. The antibody crossreacts 100% with Ang II and its C-terminal fragments Ang-(2-8), Ang-(3-8) and Ang-(4-8) but showed less than 0.01% binding with either Ang I or Ang-(1-7) fragments. The sensitivity of the Ang II RIA is 0.5 fmol/tube. The antibody of Ang-(1-7) (Core No. 1) was obtained in the inventors laboratory. (Chappell MC, Brosnihan KB, Diz DI, Ferrario CM: *Identification of Angiotensin-(1-7) in Rat Brain: Evidence for Differential Processing of Angiotensin Peptides.* J. Biol. Chem. 288:16518–16523,1989; and, Kohara K, Brosnihan KB, Chappell MC, Khosla MC, Ferrario CM: *Angiotensin-(1-7): A Member of Circulating Angiotensin pep-*

*tides.* Hypertension, 17:131–138,1991). It shows 100% cross-reactivity with Ang-(1-7) and Ang-(2-7), but does not recognize either Ang I or Ang II. The sensitivity of this assay is 4 fmol/tube. The identity of the Ang peptides by HPLC of a pool sample of rat blood, was verified as described previously (Chappell MC, Brosnihan KB, Diz DI, Ferrario CM: *Identification of Angiotensin-(1-7) in Rat Brain: Evidence for Differential Processing of Angiotensin Peptides.* J. Biol. Chem. 288:16518–16523,1989; and, Kohara K, Brosnihan KB, Chappell MC, Khosla MC, Ferrario CM: Angiotensin-(1-7): *A Member of Circulating Angiotensin Peptides.* Hypertension 17:131-138,1991). For data analysis, non-detectable values were assigned the value of the sensitivity of the assay.

Materials:

SCH 39,370 was kindly provided by Dr. E. J. Sybertz (Schering-Plough Research, Bloomfield, N.J.). The inhibitor was dissolved in a mixture of 2.0 N NaOH and heparinized saline. MK-422 was a gift from Merck, Inc. (Rahway, N.J.). Z-pro-prolinal was made and kindly provided by Dr. S. Wilk (Mount Sinai University, New York, N.Y.). Ang I was purchased from Bachem, Inc. (Torrance, Calif.).

Statistical Analysis

Differences resulting from drug treatments were evaluated by one-way analysis of variance followed by Duncan's multiple range test. Comparison among the five groups over all time points were done by two-way analysis of variance with repeated measures. All data are mean±SEM. The criterion for statistical significance is $p < 0.05$.

Results

Baseline levels of Ang I were not different between WKY (0.11±0.04 pmol/ml) vs SHR (0.08±0.02 pmol/ml). At baseline, Ang II and Ang-(1-7) were near or below the detectable level of the assay, due to the small volume of blood withdrawn. The pattern of clearance of Ang I in blood of control rats is shown in FIGS. 12A–12D. Corresponding changes in blood levels of Ang II and Ang-(1-7) are illustrated in FIGS. 13A–13D and 14A–14D, respectively. In all experiments peak levels of Ang peptide concentrations were observed in the first sample taken 15 seconds after injection of Ang I. In control rats peak increases in the concentration of Ang I were 3.8±0.5 pmol/ml in WKY and 4.9±0.9 pmol/ml in SHR. This difference was not statistically significant ($p > 0.05$). Fifteen seconds after Ang I injection, levels of Ang II averaged 11.5±2.1 pmol/ml in WKY and 13.1±2.2 pmol/ml in SHR ($p > 0.05$). In contrast, levels of Ang-(1-7) between 15 seconds and 60 seconds after injection of Ang I were significantly greater in SHR as assessed by two-way analysis of variance ($p < 0.05$). Plasma Ang-(1-7) at 15 seconds after Ang I injection averaged 0.83±0.10 pmol/ml in SHR and 0.57±0.10 pmol/ml in WKY. Peak levels of Ang-(1-7) represented 4.9% and 6.3% of Ang II concentrations in WKY and SHR, respectively. Verification that Ang I, Ang II and Ang-(1-7) were the predominant forms of circulating angiotensin was performed from analysis of plasma samples using the combination of HPLC followed by RIA.

Pretreatment with MK-422 significantly elevated baseline levels of Ang I and in both WKY (1.4±0.4 pmol/ml) and SHR (0.9±0.1 pmol/ml) and caused a significant upward shift of the time concentration clearance of Ang I in both strains of rats (FIGS. 12A–12D). This was associated with a marked inhibition of Ang II formation averaging 1% of values found in untreated WKY and SHR rats. In contrast, peak and time concentration levels of Ang-(1-7) were significantly increased in rats given MK-422 as compared to vehicle (FIGS. 14A–14D). Peak levels of Ang-(1-7) averaged 1.8±0.2 pmol/ml in WKY and 1.9±0.1 pmol/ml in SHR ($p > 0.05$). These data represent a two-fold and three-fold increase over values found in control rats (0.6±0.1 pmol/ml and 0.8±0.1 pmol/ml, $p < 0.05$). In addition, these values are 10% and 13% of peak Ang I levels in WKY and SHR, respectively.

Inhibition of NEP 24.11 produced a pattern of Ang I and Ang II metabolism that did not differ from that obtained in control rats (FIGS. 12A–12D and 13A–13D). Peak levels of Ang I were higher in SHR (6.2±0.4 pmol/ml) compared to WKY rats (4.3±0.4 pmol/ml, $p < 0.01$). Baseline levels of Ang II were significantly higher after SCH 39,370 (WKY: 0.04±0.02 pmol/ml vs 0.12±0.04 pmol/ml, $p < 0.05$; SHR: 0.02±0.02 pmol/ml vs 0.18±0.04 pmol/ml, $p < 0.05$). Likewise, peak levels of Ang II were significantly higher than in control rats ($p < 0.05$). Ang II averaged 21.8±5.4 pmol/ml in WKY and 27.2±3.8 pmol/ml in SHR ($p > 0.05$). FIGS. 14A–14D show that SCH 39,370 inhibited the formation of Ang-(1-7). Differences in time concentrations of Ang-(1-7) between vehicle and SCH 39,370 groups were statistically significant in SHR ($p > 0.01$) but not in WKY ($p > 0.05$).

Combined blockade of ACE and NEP 24.11 deceased the rate of Ang I metabolism, prevented Ang II formation and caused marked reductions in Ang-(1-7) levels in both WKY and SHR as compared to MK-422 treatment alone (FIGS. 12–14). Peak levels of Ang-(1-7) averaged 0.15±0.04 pmol/ml in WKY and 0.13±0.03 pmol/ml in SHR ($p > 0.05$). These values represented 1.1% and 0.9% of peak Ang I levels in control WKY and SHP, respectively. In rats pretreated with a combination of MK-422 and an inhibitor of prolyl endopeptidase, the injection of Ang I produced a pattern of metabolism bearing similarities to that found in rats given MK-422 alone. However, this combination of inhibitors produced levels of Ang I (FIGS. 12A–12D) and Ang-(1-7) (FIGS. 14A–14D) that were significantly below those found in WKY and SHR rats given MK-422 only ($p < 0.05$). Production of Ang II remained at levels that were close to or at the detectable level of the assay.

Discussion

The injection of Ang I into the circulation of WKY and SHR rats causes increased formation of Ang II and Ang-(1-7). Repeated sampling during the first 60 seconds after the injection of Ang I showed that levels of Ang-(1-7) were consistently greater in SHR compared to WKY controls. Conversion of Ang I into Ang-(1-7) was mediated by NEP 24.11. Furthermore, inhibition of NEP 24.11 augmented the levels of circulating Ang II, indicating an active participation of this enzyme in the degradation of Ang II. The dual role of NEP 24.11 acting both as a processing and degrading enzyme may regulate plasma levels of Ang peptides. To the inventors knowledge, this is the first in vivo demonstration of how this enzyme can affect levels of Ang peptides by cleaving the Pro[7]-Phe[8] bond of Ang I and inactivating Ang II by hydrolysis at the Tyr4-Ile[5] bond of the peptide.

The pattern of the metabolism of injected Ang I under the various conditions reveals that a dynamic equilibrium exists among angiotensin forming enzymes. Strictly speaking, the inventors see the process as a "yin-yang" mechanism. The proportional rate of conversion of Ang I into Ang-(1-7) was augmented when the formation of Ang II was blocked by inhibition of ACE. At the peak of the time concentration curve Ang-(1-7) levels in MK-422 treated WKY rats increased 307% compared to vehicle. Corresponding increases in SHR averaged 225%. At the same time the levels of Ang II were reduced by 99% in both WKY or SHR. Inhibition of NEP 24.11 reduced peak levels of Ang-(1-7) by 51% in WKY and 74% in SHR. Combined blockade of both ACE and NEP 24.11 produced peak levels of Ang-(1-7) that averaged 73% and 84% below vehicle treated WKY and SHR, respectively. Neither SCH 39,370 alone or in combination with MK-422 blocked the formation of Ang-(1-7) in its entirety. In preliminary experiments larger doses of SCH 39,370 caused no further inhibition of Ang-(1-7) production. In addition, the inventors found no evidence for a contribution by prolyl endopeptidase. Therefore, another enzyme(s) may contribute to the formation of the heptapeptide in the circulation of WKY and SHR. These findings show that there are multiple metabolic pathways for Ang-I.

NEP 24.11 degrades both atrial natriuretic peptide (ANP) and kinins (Roques BP, Beaumont A: *Neutral Endopeptidase- 24.11 Inhibitors: From Analgesics to Antihypertensive?* Trends in Pharmacol. Sci. 211:245-249,1990; and, Gafford JT, Skidgel A, Erdos EG, Hersh LB: *Human Kidney "Enkephalinase", a Neutral Metalloendopeptidase that Cleaves Active Peptides.* Biochemistry 22:3265-3271,1983). The above findings suggest that this endopeptidase also influences the metabolism of Ang I by decreasing hydrolysis of Ang II and facilitating conversion of Ang I into Ang-(1-7). Inhibition of Ang II degradation appears to be an important action of SCH 39,370. In the inventors experiments, SCH 39,370 caused both baseline and peak plasma levels of Ang II to double in both WKY and SHR. Gafford et al. have reported that NEP 24.11 hydrolyzes Ang II at the $Tyr^4$, $Ile^5$ to yield Ang-(1-4) (Gafford JT, Skidgei A, Erdos FG, Hersh LB: *Human Kidney "Enkephalinase", a Neutral Metalioendopeptidase that Cleaves Active Peptides.* Biochemistry 22:3265-3271,1983.). Therefore, the observation that SCH 39,370 did not reduce blood pressure in SHR may reflect the opposing effects that NEP 24.11 has on the various peptidergic systems that regulate vascular resistance. SCH 39,370 has antihypertensive effects in DOCA-salt hypertensive rats. Because this form of hypertension is associated with suppression of the peripheral renin angiotensin system, the vasodilator effects of the inhibitor may not be masked by the counter-balancing actions of NEP 24.11 on Ang I metabolism. The inventors also confirmed that conversion of Ang I into Ang-(1-7) is not dependent upon an intermediate production of Ang II. In MK-422 treated animals inhibition of Ang II production was associated with increased levels of Ang-(1-7).

The inventors studies also showed that metabolism of Ang I into Ang-(1-7) is regulated by several distinct enzymatic pathways in both the blood and in the tissues. In both canine hypothalamic homogenates and NG108 cells, prolyl endopeptidase accounted for 40% of the Ang-(1-7) generating activity. NEP 24.11 was not involved in the metabolism of Ang I in these tissue since production of Ang-(1-7) was not inhibited in the presence of phosphoramidon. Both this and previous studies agree with the inventors suggestion that metabolic pathways contributing to the generation of Ang peptides are tissue specific (Ferrario CM, Brosnihan KB, Diz DI, Jaiswal N, Khosla MC, Milsted A, Tallant EA: *Angiotensin-(1-7): A New Hormone of the Angiotensin System.* Hypertension 18: (Suppl III): III-126-133,1991.) Diversification of peptide processing arises from different enzymes contributing to alternate pathways for angiotensin metabolism.

Although in a qualitative fashion the metabolism of Ang I over time in SHR and WKY was similar, the inventors findings revealed interesting differences. Production of Ang-(1-7) was augmented in SHR after injection of Ang I. These data are in agreement with the inventors preliminary finding wherein increased plasma levels of Ang-(1-7) but not Ang II in the arterial blood of mature SHR (Kohara K, Brosnihan KB, Ferrario CM: *Angiotensin-(1-7) in the Spontaneously Hypertensive Rat.* Circulation 84 (Suppl II): 11-662,1991) were found. In addition, injection of Ang I elicited significantly smaller increases in the peak and time concentration clearance of Ang I in SHR rats treated with MK-422. These data suggest altered pathways of Ang I metabolism in hypertensive animals.

In addition, the data also suggests that NEP 24.11 has a major role in the in vivo metabolism of Ang I in the circulation of WKY and SHR. This endopeptidase acts on Ang I to form Ang-(1-7) and contribute to the degradation of Ang II. Moreover, the results indicate that SCH 39,370 is an effective inhibitor for Ang-(1-7) formation.

EXAMPLE 8

Evidence that the Metalloendopeptidase 3.4.24.15 Participates in the Conversion of Ang I to Ang-(1-7) and that cFP-AAF-pAB is an Effective Inhibitor of Ang-(1-7) Formation The metabolism of angiotensin (Ang) peptides was studied in vascular smooth muscle cultures (VSMC) from spontaneously hypertensive and normotensive rats. Because earlier studies showed that the serine endopeptidase (prolyl endopeptidase (EP)) accounted for 30% to 40% of the Ang-(1-7) production, the inventors sought to identify the remaining proteolytic activity that formed Ang-(1-7) from Ang I. In these experiments, 0.4 nM of either $^{125}$I-Ang I was incubated with intact cell monolayers and the medium was analyzed for $^{125}$I-products by high performance liquid chromatography. The major product generated from the metabolism of labeled Ang I was identified as the aminoterminal heptapeptide Ang-(1-7). Carboxyphenylpropyl-alanyl-alanyl-phenylalanyl-para-aminiobenzoate (cFP-AAF-pAB), a specific inhibitor of endopeptidase 3.4.24.15, inhibited the formation of Ang-(1-7) from Ang-I by 90% in both the spontaneously hypertensive and normotensive rats. The converting enzyme inhibitor enalaprit (MK-422) had no effect on the levels of Ang-(1-7). These findings demonstrate a preferential processing of Ang-I into Ang-(1-7) which is not dependent on the prior formation of Ang II.

Method and Materials

Cell cultures

Aortic smooth muscle cells were isolated according to the following general process. The adventia and outer third medial layer were removed from segments (2 cm$^2$) of the thoracic aorta from SHR or WYK rats, minced into 1 cm$^2$ pieces and allowed to adhere on plastic for 15 minutes. The explants were incubated with Dulbecco's modified Eagles' medium (DMEM, Irvine Scientific CO., Irvine, Calif.) diluted 1:1 with F12 (Irvine Scientific) and supplemented with 10% fetal calf serum and 1% penicillin/streptomyocin in a humid atmosphere of 95% air, 5% $CO_2$ at 37° five days and the tissues were removed after a halo of cells appeared around the explant. At confluency, the cells were harvested with 0.01% trypsin/0.02% EDTA in saline, split 1:3 for passage in 75 $cm^2$ flasks or 24 well plates and grown to confluency. The culture medium was changed daily for the three days and thereafter, every third day. The smooth muscle cells were evaluated both for their morphological appearance and their recognition of a monoclonal antibody to smooth muscle-type alpha actin (A 2547, Sigma Chemical, St. Louis, MO).

Cell Metabolism

For metabolism studies, cell monolayers (passage 4 to 6) in 24 well plates were washed twice with 1.0 ml of Krebs-Ringer solution (125 mM NaCl, 5 mM KCl, 1.0 mM $CaCl_2$, 1.2 mM $MgSO_4$, 25 mM HEPES, pH 7.4 and 6 mM glucose). Intact cells were incubated with $^{125}$I-Ang I (0.2-0.4 nM, final concentration) both in the presence and absence of enzyme inhibitors in 0.25 ml of Krebs buffer at 37° C. At selected time points, aliquots (0.05 ml) were withdrawn from the well, diluted in 0.15 ml 80% acetonitrile (ACN)/0.2% heptafluorobutyric acid (HFBA) stored at −80° C. prior to analysis by high performance liquid chromatography (HPLC). In addition, 0.20 ml of the medium, exposed to the cells for 60 minutes were incubated with $^{125}$I-Ang I for 60-120 minutes at 37° C. and analyzed by HPLC.

After the incubation, VSMC plates were placed on ice and washed twice with 1 ml Krebs-Ringer buffer at 4° C. The amount of radioligand bound to the extracellular surface was determined by dissociation with 0.5 ml glycine, 150 mM NaCl for 10 minutes on ice. The identity of intracellular radiolabel was then determined by dissolving the cells in 80% ACN/0.2% HFBA, $C_{18}$ extraction, and HPLC analysis.

Lactate dehydrogenase (LDH) was measured on a Technicon SMA II Autoanalyzer (Tarrytown, N.Y.). The presence of LDH was determined in the incubation media with and without inhibitors and compared to the total concentration of LDH in the cells. Extracellular LDH activity ranged from 0.1-0.5% in comparison to total cellular LDH for both control and inhibitor-treated cells.

HPLC Analysis $^{125}$I-products were characterized by HPLC using a heptafluorobutyric acid (HFBA) solvent system. This system consisted of 0.13% HFBA (mobile phase A) and 80% ACN/0.13% HFBA (mobile phase B) and the analysis was performed on a Kratos 400 HPLC equipped with a Waters Nova-Pak $C_{18}$ column (Waters, MA, 2.1×15 mm) and an Aquapore column (Waters, MA, 2.1×15 mm) and an Aquapore $C_8$ guard column (Applied Biosystems, 3.2×1.5 mm). The gradient conditions consisted of 20-50% B Linear (30 min) and 50% B isocratic (10 min) at a flow rate of 0.3 ml/min at room temperature. HPLC fractions were collected every 0.5 min and counted in a gamma counter. Products were identified by comparison of their retention times to those of standard $^{125}$I-angiotensin peptides. To further assess the identity of each radioactive peak, either the incubation samples or $^{125}$I-products were rechromatographed using a trifluoracetic acid (TFA) solvent. This system consisted of 0.1% TFA, pH 4.5 (mobile phase A) and 60% ACN/0.1% TFA pH 4.5 (mobile phase B). A linear gradient of 15-45% B (30 min) and 45% B isocratic (10 min) at 0.3 ml/min at room temperature was performed on the HPLC system described above.

Prostaglandin Assay

The release of $PGI_2$ (measured as the stable metabolite 6-keto-$PGF_{1a}$) was determined by radioimmunoassay with an antibody kindly provided by Dr. K. U. Malik (Dept. of Pharmacology, Univ. of Tennessee, Memphis, Tenn.). The 6-keto-$PGF_{1a}$ antibody cross-reacts <0.5% with thromboxane B2, 13,14 dihydro-15-ketoPGE2 and $PFG2_a$ and does not crossreact with Ang 1-7. Samples (0.1 ml) of the cell incubation medium were added to 3,000 cpm of [$^3$H]6-keto-$PGF_{1a}$ and antibody for 2 hours. The bound trace was isolated by addition of 1.0 ml dextran-coated charcoal, centrifuged, and the radioactive pellet was counted by liquid-scintillation spectroscopy.

SDS-Western Blots

Angiotensin peptides were provided by Bachem, Inc. (Torrance, Calif.). $^{125}$I-Ang I and other Ang peptides were iodinated using the modified chloramine T procedure and purified by HPLC (specific activity: 2200 Curies/mmol). [$^3$H]6-keto-PGF1 was purchased from Du Pont-New England Nuclear (Boston, Mass.). Carboxy-phenylpropyl-alanyl-alanyl-phenylalanyl-para-aminiobenzoate (cPF-AAF-pAB), a specific inhibitor of neutral endopeptidase EC 3.4.24.15 (NEP 24.15) and N-benzyloxycarbonyl-prolylprolinal (ZPP), a specific inhibitor of prolyl endopeptidase (EC 3.4.21.26,PE) were generous gifts from Drs. M. Orlowski and S. Wilk (Dept. of Pharmacology, Mount Sinai School of Medicine, New York). Enalaprilat (MK-422), a CE inhibitor, was a gift from Merck Inc. (Rahway, N.J.). Thiorphoran, an inhibitor of neutral endopeptidase EC 3.4.24.11 (NEP 24.11), bestatin, an aminopeptidase inhibitor, and p-chloromercuriphenylsulfonate acid (PMSF), a cysteine protease inhibitor, were obtained from Sigma. HFBA (Sequanal Grade) and TFA (HPLC Grade) were obtained from Pierce (Rockford, Ill.) and ACN (Burdick and Jackson) was purchased from American Scientific (Columbus, Ohio).

Statistics: Differences in the generation of $^{125}$I-peptides under various conditions were assessed by analyses of variance followed by Newman Keuls multiple comparison test. The criterion for statistical significance was set at $p < 0.05$.

Results

Peptide Metabolism

After a 30 minute exposure of $^{125}$I-Ang I to the cells, $^{125}$I-Ang-(1-7) was identified as the main peptide product in the medium using the HFBA solvent system. In addition, several other radioactive metabolites were also detected at this time point. These $^{125}$I-products eluted with retention times corresponding to $^{125}$I-Ang-(1-4), $^{125}$I-Val-Tyr, and $^{125}$I-Tyr standards. Although $^{125}$I-Ang II was well separated by the chromatographic system, the generation of this peptide was not observed at any time point during the incubation of $_{125}$I-Ang with either the SHR or WKY cultures. To verify the identity of the $^{125}$I-Ang-(1-7) product, the radioactive peak corresponding to $^{125}$I-Ang-(1-7) from the first chromatograph was rechromatographed on the TFA solvent system. The radioactive peak eluted with a retention time identical to that of the $^{125}$I-Ang-(1-7) standard.

The time course for the metabolism of $^{125}$I-Ang I in VSMC from SHR rats was also determined. From 5 to 30 min, the level of $^{125}$I-Ang-(1-7) increased from approximately 20% to 45% of the total amount of radioactive peptides. During this time period $^{125}$I-Ang-(1-7) generation accounted for at least 65% to 80% of the total $^{125}$I-Ang I metabolism. After 30 min, the level of $^{125}$I-Ang-(1-7) gradually declined suggesting that the catabolism of this peptide may exceed its generation. Coincident with the decline in $^{125}$I-Ang-(1-7), the inventors observed an increase in the level of other fragments including $^{125}$I-Tyr and $^{125}$I-Ang-(1-4). A similar time course as well as identical products from the metabolism of $^{125}$I-Ang I was obtained in the WKY cultures.

Peptidase Characterization

Since formation of $^{125}$I-Ang-(1-7) accounted for the majority of $^{125}$I-Ang I metabolism, the characterization of $^{125}$-I-Ang-(1-7) formation was undertaken. Shown in FIG. 15 are the effects of various inhibitors on the levels of 125I-Ang-(1-7) from the VSMC of the SHR and WKY rats. The converting enzyme inhibitor MK-422 (10μM) did not have an effect on the levels of $^{125}$I-Ang-(1-7). These data suggest that the majority of $^{125}$I-Ang-(1-7) generation was not dependent on prior formation of $^{125}$I-Ang II. Although both PE 26.14 and EP 24.11 are capable of cleaving the Pro$^7$-Phe$^8$ bond of Ang I to yield Ang-(1-7), 10 μM ZPP (PE inhibitor) or 10 μM thiorphan (EP 24.11 inhibitor) had no effect on $^{125}$I-Ang-(1-7) levels. However, addition of the EP 24.15 inhibitor cPf-AAF-pAB (10 μM) decreased the formation of $^{125}$I-Ang-(1-7) by over 90% in both the SHR and WKY cultures. Moreover, inclusion of the cysteine protease inhibitor PCMS (1 μM) inhibited $^{125}$I-Ang-(1-7) levels to a similar extent as that observed with cPF-AAF-pAB (data not shown). EP 24.15 has been classified as a metalloendopeptidase, however, the enzyme is particularly sensitive to mercurial inhibitors such as PCMS.

Discussion

The present study reveals that intact VSMC from both SHR and WKY rats can process extracellular $^{125}$I-Ang I into $^{125}$I-Ang-(1-7). However, the above results indicate that $^{125}$I-Ang-(1-7) is the primary product from $^{125}$I-Ang-(1-7) and that the formation of $^{125}$I-Ang-(1-7) is not dependent on the prior generation of $^{125}$I-Ang II. This novel finding suggests that in these cells the formation of $^{125}$I-Ang-(1-7) is apparently favored over that of $^{125}$I-AngII. Furthermore the results disclose that NEP 24.15 is a major Ang-(1-7)forming enzyme in VSMC and that cFP-AAF-pAB is an effective inhibitor for Ang-(1-7) formation.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims and the equivalents thereof.

Having thus described the preferred embodiment, the invention is now claimed to be:

1. A process for reducing hypertension in mammals which comprises administering Z-Proprolinal to a hypertensive mammal in an amount effective to reduce hypertension.

2. The process of claim 1 wherein said Z-Proprolinal is administered to the renin-angiotensin system of the mammal.

3. The process of claim 1 wherein said Z-Proprolinal is administered to the brain renin-angiotensin system of the mammal.

4. The process of claim 1 wherein said Z-Proprolinal is administered to the hypothalamic region of the mammal.

5. The process of claim 1 wherein said mammal is a dog.

6. The process of claim 1 wherein said mammal is a rat.

7. A process for reducing the blood pressure in mammals which comprises administering Z-Pro-prolinal to a mammal in an amount effective to reduce the blood pressure of said mammal.

8. The process of claim 7 wherein said Z-Proprolinal is administered to the renin-angiotensin system of the mammal.

9. The process of claim 7 wherein said Z-Proprolinal is administered to the brain renin-angiotensin system of the mammal.

10. The process of claim 7 wherein said Z-Proprolinal is administered to the hypothalamic region of the mammal.

11. The process of claim 7 wherein said mammal is a dog.

12. The process of claim 7 wherein said mammal is a rat.

* * * * *